US011840720B2

(12) United States Patent
Deng et al.

(10) Patent No.: US 11,840,720 B2
(45) Date of Patent: Dec. 12, 2023

(54) URINARY METABOLOMIC BIOMARKERS FOR DETECTING COLORECTAL CANCER AND POLYPS

(71) Applicant: Metabolomic Technologies Inc., Edmonton (CA)

(72) Inventors: Lu Deng, Edmonton (CA); David Chang, Edmonton (CA)

(73) Assignee: Metabolomic Technologies Inc., Edmonton (CA)

( * ) Notice: Subject to any disclaimer, the term of this patent is extended or adjusted under 35 U.S.C. 154(b) by 552 days.

(21) Appl. No.: 16/725,914

(22) Filed: Dec. 23, 2019

(65) Prior Publication Data
US 2021/0189499 A1 Jun. 24, 2021

(51) Int. Cl.
G01N 33/48 (2006.01)
C12Q 1/6886 (2018.01)
G01N 33/493 (2006.01)
G01N 33/49 (2006.01)
A61K 45/06 (2006.01)
G01N 33/574 (2006.01)

(52) U.S. Cl.
CPC ......... *C12Q 1/6886* (2013.01); *G01N 33/492* (2013.01); *G01N 33/493* (2013.01); *A61K 45/06* (2013.01); *C12Q 2600/106* (2013.01); *C12Q 2600/158* (2013.01); *G01N 33/57419* (2013.01); *G01N 2800/50* (2013.01); *G01N 2800/52* (2013.01); *G01N 2800/7028* (2013.01)

(58) Field of Classification Search
CPC ... C12Q 1/6886; G01N 33/492; G01N 33/493
See application file for complete search history.

(56) References Cited

U.S. PATENT DOCUMENTS

| | | |
|---|---|---|
| 6,423,491 B1 | 7/2002 | Howe et al. |
| 7,553,616 B2 | 6/2009 | Kaddurah-Daouk et al. |
| 9,134,313 B2 | 9/2015 | Kawakita et al. |
| 10,006,925 B2 | 6/2018 | Bitenc et al. |
| 10,267,777 B2 | 4/2019 | Milburn et al. |
| 10,274,496 B2 | 4/2019 | Raftery et al. |
| 10,487,363 B2 | 11/2019 | Manna et al. |
| 2007/0178599 A1 | 8/2007 | Kaddurah-Daouk et al. |
| 2007/0161059 A1 | 12/2007 | Kawakita et al. |
| 2008/0255764 A1 | 10/2008 | Ritchie et al. |
| 2009/0075284 A1 | 3/2009 | Chinnaiyan et al. |
| 2012/0040383 A1 | 2/2012 | Jia et al. |
| 2012/0197539 A1 | 8/2012 | Slupsky |
| 2013/0065320 A1 | 3/2013 | Fedorak et al. |
| 2015/0065366 A1 | 3/2015 | McDunn et al. |
| 2016/0282351 A1 | 9/2016 | Sugimoto et al. |
| 2018/0180618 A1 | 6/2018 | Bux et al. |

FOREIGN PATENT DOCUMENTS

| | | |
|---|---|---|
| JP | 2009508091 A | 2/2009 |
| WO | 2007088537 A2 | 8/2007 |
| WO | 2008075663 A1 | 6/2008 |
| WO | 2009037572 A2 | 3/2009 |
| WO | 2011041892 A1 | 4/2011 |
| WO | 2011136343 A1 | 11/2011 |
| WO | 2011143779 | 11/2011 |
| WO | 2017165956 A1 | 10/2017 |
| WO | 2018184112 A1 | 10/2018 |
| WO | 2019224542 A1 | 11/2019 |
| WO | 2020023630 A1 | 1/2020 |

OTHER PUBLICATIONS

Sugimoto et al., J Cancer Res Clin Oncol., 1995, 121:317-319.*
Deng et al., American J of Gastroenterology, 2018, 113: p. S153.*
Zhang et al., Anal. Chem., 2018, 90:11941-11948.*
Levin TR, Corley DA, Jensen CD, Schottinger JE, Quinn VP, Zauber AG, et al. Effects of Organized Colorectal Cancer Screening on Cancer Incidence and Mortality in a Large Community-Based Population. Gastroenterology 2018 doi 10.1053/j.gastro.2018.07.017.
Dube C. Organized screening is better than opportunistic screening at decreasing the burden of colorectal cancer in the United States. Gastroenterology 2018;155(5):1302-4 doi 10.1053/j.gastro.2018.10.010.
Navarro M, Nicolas A, Ferrandez A, Lanas A. Colorectal cancer population screening programs worldwide in 2016: An update. World J Gastroenterol 2017;23(20):3632-42 doi 10.3748/wjg.v23.120.3632.
Schreuders EH, Ruco A, Rabeneck L, Schoen RE, Sung JJ, Young GP, et al. Colorectal cancer screening: a global overview of existing programmes. Gut 2015;64(10):1637-49 doi 10.1136/gutjnl-2014-309086.
Imperiale TF, Ransohoff DF, Itzkowitz SH, Levin TR, Lavin P, Lidgard GP, et al. Multitarget Stool DNA Testing for Colorectal-Cancer Screening. New England Journal of Medicine 2014;370(14):1287-97 doi 10.1056/NEJMoa1311194.
Quintero E, Castells A, Bujanda L, Cubiella J, Salas D, Lanas A, et al. Colonoscopy versus fecal immunochemical testing in colorectal-cancer screening. N Engl J Med 2012;366(8):697-706 doi 10.1056/NEJMoa1108895.
Van Roon AH, Goede SL, van Ballegooijen M, van Vuuren AJ, Looman CW, Biermann K, et al. Random comparison of repeated faecal immunochemical testing at different intervals for population-based colorectal cancer screening. Gut 2013;62(3):409-15 doi 10.1136/gutjnl-2011-301583.

(Continued)

*Primary Examiner* — Bin Shen

(74) *Attorney, Agent, or Firm* — Troutman Pepper Hamilton Sanders LLP

(57) ABSTRACT

The invention relates to methods and compositions for detecting colorectal cancer and colorectal polyps by measurement of metabolites in bodily fluids such as urine, including diacetylspermine and kynurenine.

16 Claims, 10 Drawing Sheets

(56) References Cited

OTHER PUBLICATIONS

Zubero MB, Arana-Arri E, Pijoan JI, Portillo I, Idigoras I, Lopez-Urrutia A, et al. Population-based colorectal cancer screening: comparison of two fecal occult blood test. Frontiers in pharmacology 2014;4:175 doi 10.3389/fphar.2013.00175.
Singh H, Bernstein CN, Samadder JN, Ahmed R. Screening rates for colorectal cancer in Canada: a cross-sectional study. CMAJ open 2015;3(2):E149-57 doi 10.9778/cmajo.20140073.
Singal AG, Corley DA, Kamineni A, Garcia M, Zheng Y, Doria-Rose PV, et al. Patterns and predictors of repeat fecal immunochemical and occult blood test screening in four large health care systems in the United States. Am J Gastroenterol 2018;113(5):746-54 doi 10.1038/s41395-018-0023-x.
Church J. Complications of Colonoscopy. Gastroenterology Clinics of North America 2013;42(3):639-57 doi 10.1016/j.gtc.2013.05.003.
Dougherty MK, Brenner AT, Crockett SD, Gupta S, Wheeler SB, Coker-Schwimmer M, et al. Evaluation of Interventions Intended to Increase Colorectal Cancer Screening Rates in the United States: A Systematic Review and Meta-analysis. JAMA internal medicine 2018 doi 10.1001/jamainternmed.2018.4637.
Cossu G, Saba L, Minerba L, Mascalchi M. Colorectal Cancer Screening: The Role of Psychological, Social and Background Factors in Decision-making Process. Clinical practice and epidemiology in mental health : CP & EMH 2018;14:63-9 doi 10.2174/1745017901814010063.
Osborne JM, Flight I, Wilson CJ, Chen G, Ratcliffe J, Young GP. The impact of sample type and procedural attributes on relative acceptability of different colorectal cancer screening regimens. Patient preference and adherence 2018;12:1825-36 doi 10.2147/ppa.S172143.
Liles EG, Coronado GD, Perrin N, Harte AH, Nungesser R, Quigley N, et al. Uptake of a colorectal cancer screening blood test is higher than of a fecal test offered in clinic: A randomized trial. Cancer Treatment and Research Communications 2017;10:27-31 doi https://doi.org/10.1016/j.ctarc.2016.12.004.
Lamb YN, Dhillon S. Epi proColon((R)) 2.0 CE: A Blood-Based Screening Test for Colorectal Cancer. Molecular diagnosis & therapy 2017;21(2):225-32 doi 10.1007/s40291-017-0259-y.
Anabtawi A, Mathew LM. Improving compliance with screening of diabetic patients for microalbuminuria in primary care practice. ISRN endocrinology 2013;2013:893913 doi 10.1155/2013/893913.
Oboler SK, Prochazka AV, Gonzales R, Xu S, Anderson RJ. Public expectations and attitudes for annual physical examinations and testing. Annals of internal medicine 2002;136(9):652-9.
Widlak MM, Neal M, Daulton E, Thomas CL, Tomkins C, Singh B, et al. Risk stratification of symptomatic patients suspected of colorectal cancer using faecal and urinary markers. Colorectal disease : the official journal of the Association of Coloproctology of Great Britain and Ireland 2018 doi 10.1111/codi.14431.
Guo C, Xie C, Chen Q, Cao X, Guo M, Zheng S, et al. A novel malic acid-enhanced method for the analysis of 5-methyl-2'-deoxycytidine, 5-hydroxymethyl-2'-deoxycytidine, 5-methylcytidine and 5-hydroxymethylcytidine in human urine using hydrophilic interaction liquid chromatography-tandem mass spectrometry. Analytica chimica acta 2018;1034:110-8 doi 10.1016/j.aca.2018.06.081.
Nakajima T, Katsumata K, Kuwabara H, Soya R, Enomoto M, Ishizaki T, et al. Urinary Polyamine Biomarker Panels with Machine-Learning Differentiated Colorectal Cancers, Benign Disease, and Healthy Controls. International journal of molecular sciences 2018;19(3) doi 10.3390/ijms19030756.
Venalainen MK, Roine AN, Hakkinen MR, Vepsalainen JJ, Kumpulainen PS, Kiviniemi MS, et al. Altered Polyamine Profiles in Colorectal Cancer. Anticancer research 2018;38(6):3601-7 doi 10.21873/anticanres.12634.
Wang H, Tso V, Wong C, Sadowski D, Fedorak RN. Development and validation of a highly sensitive urine-based test to identify patients with colonic adenomatous polyps. Clin Transl Gastroenterol 2014;5:e54 doi 10.1038/ctg.2014.2.
Deng L, Chang D, Foshaug RR, Eisner R, Tso VK, Wishart DS, et al. Development and Validation of a High-Throughput Mass Spectrometry Based Urine Metabolomic Test for the Detection of Colonic Adenomatous Polyps. Metabolites 2017;7(3):32 doi 10.3390/metabo7030032.
Deng L, Fang H, Tso VK, Sun Y, Foshaug RR, Krahn SC, et al. Clinical validation of a novel urine-based metabolomic test for the detection of colonic polyps on Chinese population. Int J Colorectal Dis 2017;32(5):741-3 doi 10.1007/s00384-016-2729-9.
Tso V ER, Macleod S, Ismond KP, Foshaug RR, Wang H, Joseph R, Chang D, Taylor N and Fedorak RN. Consistency of Metabolite Determination from NMR Spectra over Time and Between Operators. Metabolomics 2015;5(3):151 doi 10.4172/2153-0769.1000151.
Eisner R, Greiner R, Tso V, Wang H, Fedorak RN. A machine-learned predictor of colonic polyps based on urinary metabolomics. Biomed Res Int 2013;2013:303982 doi 10.1155/2013/303982.
Wong CK, Fedorak RN, Prosser CI, Stewart ME, van Zanten SV, Sadowski DC. The sensitivity and specificity of guaiac and immunochemical fecal occult blood tests for the detection of advanced colonic adenomas and cancer. Int J Colorectal Dis 2012;27(12):1657-64 doi 10.1007/s00384-012-1518-3.
R Core Team. 2018 R: A Language and Environment for Statistical Computing. R Foundation for Statistical Computing <https://www.R-project.org>.
Chong J, Soufan O, Li C, Caraus I, Li S, Bourque G, et al. MetaboAnalyst 4.0: towards more transparent and integrative metabolomics analysis. Nucleic Acids Research 2018;46(W1):W486-W94 doi 10.1093/nar/gky310.
Altobelli E, Angeletti PM, Latella G. Role of Urinary Biomarkers in the Diagnosis of Adenoma and Colorectal Cancer: A Systematic Review and Meta-Analysis. Journal of Cancer 2016;7(14):1984-2004 doi 10.7150/jca.16244.
Qiu G, Zheng Y, Wang H, Sun J, Ma H, Xiao Y, et al. Plasma metabolomics identified novel metabolites associated with risk of type 2 diabetes in two prospective cohorts of Chinese adults. International Journal of Epidemiology 2016;45(5):1507-16 doi 10.1093/ije/dyw221.
Stoessel D, Stellmann J-P, Willing A, Behrens B, Rosenkranz SC, Hodecker SC, et al. Metabolomic Profiles for Primary Progressive Multiple Sclerosis Stratification and Disease Course Monitoring. Frontiers in human neuroscience 2018;12:226—doi 10.3389/fnhum.2018.00226.
Delplancke TDJ, de Seymour JV, Tong C, Sulek K, Xia Y, Zhang H, et al. Analysis of sequential hair segments reflects changes in the metabolome across the trimesters of pregnancy. Scientific reports 2018;8(1):36—doi 10.1038/s41598-017-18317-7.
Lê Cao K-A, Boitard S, Besse P. Sparse PLS discriminant analysis: biologically relevant feature selection and graphical displays for multiclass problems. BMC Bioinformatics 2011;12(1):253 doi 10.1186/1471-2105-12-253.
Friedman JH, Hastie T, Tibshirani R. Regularization Paths for Generalized Linear Models via Coordinate Descent. Journal of Statistical Software 2010;33(1):1-22 doi 10.18637/jss.v033.101.
Sing T, Sander O, Beerenwinkel N, Lengauer T. ROCR: visualizing classifier performance in R. Bioinformatics 2005;21(20):3940-1 doi 10.1093/bioinformatics/bti623.
Spacek M. Kynurenine in disease, with particular reference to cancer. Canadian Medical Association journal 1955;73(3):198-201.
Enjoji M, Nakamuta M, Arimura E, Morizono S, Kuniyoshi M, Fukushima M, et al. Clinical significance of urinary N1, N12-diacetylspermine levels in patients with hepatocellular carcinoma. The International journal of biological markers 2004;19(4):322-7.
Hiramatsu K, Takahashi K, Yamaguchi T, Matsumoto H, Miyamoto H, Tanaka S, et al. N(1),N(12)-Diacetylspermine as a sensitive and specific novel marker for early- and late-stage colorectal and breast cancers. Clinical cancer research : an official journal of the American Association for Cancer Research 2005;11(8):2986-90 doi 10.1158/1078-0432. Ccr-04-2275.
Yamaguchi K, Nakamura M, Shirahane K, Konomi H, Torata N, Hamasaki N, et al. Urine diacetylspermine as a novel tumour maker

(56) References Cited

OTHER PUBLICATIONS for pancreatobiliary carcinomas. Digestive and liver disease : official journal of the Italian Society of Gastroenterology and the Italian Association for the Study of the Liver 2005;37(3):190-4 doi 10.1016/j.dld.2004.10.006.
Takahashi Y, Sakaguchi K, Horio H, Hiramatsu K, Moriya S, Takahashi K, et al. Urinary N1, N12-diacetylspermine is a non-invasive marker for the diagnosis and prognosis of non-small-cell lung cancer. Br J Cancer 2015;113(10):1493-501 doi 10.1038/bjc.2015.349.
Stejskal D, Humenanska V, Hanulova Z, Fiala R, Vrtal R, Solichova P, et al. Evaluation of urine N1,N12-Diacetylspermine as potential tumor marker for urinary bladder cancer. Biomed Pap Med Fac Univ Palacky Olomouc Czech Repub 2006;150(2):235-7.
Zhang F, Zhang Y, Zhao W, Deng K, Wang Z, Yang C, et al. Metabolomics for biomarker discovery in the diagnosis, prognosis, survival and recurrence of colorectal cancer: a systematic review. Oncotarget 2017;8(21):35460-72 doi 10.18632/oncotarget.16727.
Liang PS, Chen TY, Giovannucci E. Cigarette smoking and colorectal cancer incidence and mortality: systematic review and meta-analysis. International journal of cancer 2009;124(10):2406-15 doi 10.1002/ijc.24191.
Bathe OF, Shaykhutdinov R, Kopciuk K, Weljie AM, McKay A, Sutherland FR, et al. Feasibility of identifying pancreatic cancer based on serum metabolomics. Cancer Epidemiology Biomarkers & Prevention 2011;20(1):140-7 doi 10.1158/1055-9965.Epi-10-0712.
Ni Y, Xie G, Jia W. Metabonomics of Human Colorectal Cancer: New Approaches for Early Diagnosis and Biomarker Discovery. Journal of Proteome Research 2014;13(9):3857-70 doi 10.1021/pr500443c.
Erben V, Bhardwaj M, Schrotz-King P, Brenner H. Metabolomics biomarkers for detection of colorectal neoplasms: a systematic review. Cancers 2018;10(246):1-24 doi 10.3390/cancers10080246.
Trygg, J., et al., "O2-PLS, a two-block (X-Y) latent variable regression (LVR) method with an integral OSC filter," Journal of Chemometrics, 2003, vol. 17, pp. 53-64.
Trygg, J., et al., "Orthogonal projections to latent structures (O-PLS)," Journal of Chemometrics, 2002, vol. 16, pp. 119-128.
"Vapnik, V.N. (1995) The Nature of Statistical Learning Theory. New York, NY: Springer.".
Waikar and Bonventre, "Can We Rely on Blood Urea Nitrogen as a Biomarker to Determine When to Initiate Dialysis?", Clin. J. Am. Soc. Neprol., 2006, v. 1, pp. 903-906.
Wang, et al., "Development and Validation of a Highly Sensitive Urine-Based Test to Identify Patients with Colonic Adenomatous Polyps" Clinical and Translational Gastroenterology (2014) vol. 5, e54, pp. 1-8.
Wang, H., et al., "Metabolomics and detection of colorectal cancer in humans: a systematic review," Future Oncology, 2010, vol. 6(9), pp. 1395-1406.
Wang, H., et al., "The Role of NMR Urine Metabolomics as a New Method for Screening Colorectal Cancer—A Preliminary Analysis," Canadian Journal Gastroenterology, 2009, vol. 23(Supplement A):144, Canadian Digestive Diseases Week: Feb. 27-Mar. 2, 2009 in Banff, Alberta.
Wang, W., et al., "Urinary metabolic profiling of colorectal carcinoma based on online affinity solid phase extraction-high performance liquid chromatography and ultra performance liquid chromatography-mass spectrometry," Mal. BioSyst., 2010, vol. 6, pp. 1947-1955.
Want et al., "The Expanding Role of Mass Spectrometry in Metabolite Profiling and Characterization" ChemBioChem (2005) vol. 6, pp. 1941-195.
Wenzel, "Ascorbic acid suppresses drug-induced apoptosis in human colon cancer cells by scavenging mitochondrial superoxide anions", Carcinogenesis (2004) vol. 25, No. 5, pp. 703-712.
WIPO Application No. PCT/CA2011/050315, International Preliminary Report on Patentability, dated Nov. 27, 2012.
WIPO Application No. PCT/CA2011/050315, International Search Report, dated Aug. 22, 2011.

WIPO Application No. PCT/CA2011/050315, Written Opinion of the International Searching Authority, dated Aug. 22, 2011.
Wishart, D.S., "Is Cancer a Genetic Disease or a Metabolic Disease?" EBioMedicine (2015) vol. 2, pp. 478-479.
Zweig, M.H., et al., "Receiver-Operating Characteristic (ROC) Plots: A Fundamental Evaluation Tool in Clinical Medicine," Clin. Chem., 1993, vol. 39(4), pp. 561-577.
Rotter M, Brandmaier S, Prehn C, Adam J, Rabstein S, Gawrych K, et al. Stability of targeted metabolite profiles of urine samples under different storage conditions. Metabolomics 2017;13(1):4 doi 10.1007/s11306-016-1137-z.
Laparre J, Kaabia Z, Mooney M, Buckley T, Sherry M, Le Bizec B, et al. Impact of storage conditions on the urinary metabolomics fingerprint. Analytica chimica acta 2017;951:99-107 doi 10.1016/j.aca.2016.11.055.
Deng, L et al., "Clinical Validation of a Novel Urine-Based Metabolomic Test for the Detection of Colonic Polyps on Chinese Population" Int. J. Colorectal Disease (2017) vol. 32, pp. 741-743.
Office Action dated Mar. 23, 2021 in connection with Canadian Application No. 3,065,979.
Iwasaki et al., "Current status of urinary diagnostic biomarkers for colorectal cancer", Clinica Chimica Acta., vol. 498, pp. 76-83, Aug. 14, 2019.
Hiramatsu et al., "N1, N12-Diacetylspermine as a Sensitive and Specific Novel Marker for Early-and Late-Stage Colorectal and Breast Cancers", Clin. Cancer Res., 11(8), pp. 2986-2990, Apr. 15, 2005.
Huang et al., "Serum tryptophan decrease correlates with immune activiation", British J. of Cancer, 86, pp. 1691-1692, 2002.
Kuwata et al., "Increase of N-diacetylspermine in tissues from colorectal cancer and its liver metastasis1, N 12-diacetylspermine in tissues from colorectal cancer and its liver metastasis", J. of Cancer Res. & Clin. Oncology, 139 (6), pp. 925-932, Jun. 2013.
Rattray et al., "Environmental influences in the etiology of colorectal cancer: the premise of metabolomics", Curr. Pharmacl, Rep., 3(3) pp. 114-125, Jun. 2017.
International Search Report dated Oct. 11, 2018 in connection with PCT/CA2018/050421.
Dec. 8, 2021 Office Action issued in connection with Canadian Application No. 3,065,979 (No References Cited).
Ferlay J, Ervik M, Lam F, Colombet M, Mery L, Pineros M, et al. Oct. 19, 2018, 2018. Global Cancer Observatory: Cancer Tomorrow. International Agency for Research on Cancer <https://gco.iarc.fr/tomorrow>. Oct. 19, 2018 The Wayback Machine≤https://web.archive.org/web/20181004142957/http://gco.iarc.fr/today/home.
Cifuentes A. Foodomics: Advanced Mass Spectrometry in Modern Food Science and Nutrition. Wiley; 2013.
"Trigonelline in Coffee", Apr. 23, 2015: https://www.coffeechemistry.com/chemistry/alkaloids/trigonelline-incoffee?print= 1 &tmpl= component.
Allred, et al., "Trigonelline Is a Novel Phytoestrogen in Coffee Beans1 ,2" the Journal of Nutrition Biochemical, Molecular and Genetic Mechanisms (2009) No. 139, pp. 1833-1838.
Berode et al., "Urinary methanol and formic acid as indicators of occupation exposure to methyl formate", Int. Arch. Occuup. Environ. Health, 2000, v. 73, pp. 410-414.
Bond, "Colon Polyps and Cancer," Endoscopy; 35 (1):27-35, (2003).
Bouatra, S. et al., "The Human Urine Metabolome" Plos One (2013) vol. 8, Issue 9, e73076, p. 1-28.
Chan et al. "Metabolic Profiling of Human Colorectal Cancer Using High-Resolution Magic Angle Spinning Nuclear Magnetic Resonance (HR-MAS NMR) Spectroscopy and Gas Chromatography Mass Spectrometry (GC/MS)", J. Proteom. Res., 2009, v.8, pp. 352-361.
Claudino, W.M. et al., "Metabolomics: Available Results, Current Research Projects in Breast Cancer, and Future Applications" Journal of Clinical Oncology (2007) vol. 25, pp. 2840-2846.
Communication issued by the Australia Patent Office in Australian Application No. 2011256064 dated Feb. 26, 2016.
Communication issued by the Australia Patent Office in Australian Application No. 2011256064 dated Jan. 29, 2015.
Communication issued by the Australia Patent Office in Australian Application No. 2011256064 dated May 20, 2016.

(56) References Cited

OTHER PUBLICATIONS

Communication issued by the Canada Patent Office in Canada Application No. 2799757 dated May 16, 2017.
Communication issued by the Canada Patent Office in Canada Application No. 2799757 dated May 4, 2016.
Communication issued by the Canada Patent Office in Canada Application No. 2799757 dated Nov. 30, 2017.
Communication issued by the Canada Patent Office in Canada Application No. 2799757 dated Oct. 25, 2016.
Communication issued by the European Patent Office in European Application No. 11782836.8 dated Apr. 29, 2015.
Communication issued by the European Patent Office in European Application No. 11782836.8 dated Feb. 8, 2016.
Communication issued by the European Patent Office in European Application No. 11782836.8 dated Jun. 17, 2014.
Communication issued by the European Patent Office in European Application No. 11782836.8 dated Oct. 29, 2013.
Communication issued by the European Patent Office in European Application No. 11782836.8 dated Oct. 6, 2016.
Communication issued by the Japan Patent Office in Japanese Application No. 2013-510462 dated Jan. 13, 2015.
Communication issued by the Japan Patent Office in Japanese Application No. 2013-510462 dated Sep. 15, 2015.
Denkert, C., et al., "Metabolite profiling of human colon carcinoma-deregulation of TCA cycle and amino acid turnover," Molecular Cancer, 2008, vol. 7, No. 1, pp. 1-15.
Eisner, R. "A Machine-Learned Predictor of Colonic Polyps Based on Urinary Metabolomics" BioMed Research International, Hindawi Publishing Corporation (2013) Article ID 303982, pp. 1-11, 11 pages total.
EPO Application No. EP 11782836.8 (Published as EP2572193), Supplementary European Search Report and European Search Opinion, dated Nov. 20, 2013.
Eriksson, L., et al., "Multi- and Megavariate Data Analysis: Part II, Method Extensions and Advanced Applications," Umetrics Academy, 2005, Chapter 23.
Eriksson, L., et al., "Separating Y-predictive and Y-orthogonal variation in multi-block spectral data," Journal of Chemometrics, 2006, vol. 20, pp. 352-361.
Gabrielsson, J., et al., "The OPLS methodology for analysis of multi-block batch process data," Journal of Chemometrics, 2006, vol. 20, pp. 362-369.
Griner, P.F., et al., "Selection and interpretation of diagnostic tests and procedures," Principles and applications, Ann. Intern. Med., 1981, vol. 94(4 Pt 2), pp. 557-592.
Gurudu, S.R., et al., "Sessile serrated adenomas: Demographic, endoscopic and pathological characteristics," World Journal of Gastroenterology, 2010, vol. 16(27), pp. 3402-3405.
Guy et al., "Global Metabolic Profiling Analysis on Human Urine by UPLC-TOFMS: Issue and Method Validation in Nutritional Metabolomics" Journal of Chromatography B (2008) vol. 871, pp. 253-260.
Hsu, W-Y., et al., "Analysis of urinary nucleosides as potential tumor markers in human colorectal cancer by high performance liquid chromatography/electrospray ionization tandem mass spectrometry," Clinica ChimicaActa, 2009, vol. 402, pp. 31-37.
Jass, J.R., "Hyperplastic-like Polyps as Precursors of Microsatellite-Unstable Colorectal Cancer," American Journal of Clinical Pathology, 2003, vol. 119, pp. 773-775.
Joanna Karpasea-Jones, "Your Cup of Coffee Could Protect You from Colon Cancer": http://www.empowher.com/colorectal-cancer/content/your-cup-coffee-could-protect-you-colon-cancer; source: Texas Agrilife Communications Press Release, Kathleen Philips, Nov. 12, 2009.
Johnson, J.C. et al., "Urine PGE-M: A Metabolite of Prostaglandin E2 as a Potential Biomarker of Advanced Colorectal Neoplasia" Clinical Gastroenterology and Hepatology (2006) vol. 4, pp. 1358-1365.
Levin et al., "Screening and Surveillance for the Early Detection of Colorectal Cancer and Adenomatous Polyps, 2008: A Joint Guideline From the American Cancer Society, the US Multi-Society Task Force on Colorectal Cancer, and the American College of Radiology," Gastroenterology, 134: 1570-1595, (2008).
Ma, Y.-L., et al., "Ultra-High Performance Liquid Chromatography-Mass Spectrometry for the Metabolomic Analysis of Urine in Colorectal Cancer," Dig. Dis. Sci., 2009, vol. 54, pp. 2655-2662.
Muto et al., "The Evolution of Cancer of the Colon and Rectum," Cancer, 36:2251-2270, (1975).
Nambiar, P.R. et al., "An 'omics' based survey of human colon cancer" Mutation Research/Fundamental and Molecular Mechanisms of Mutagenesis (2010) vol. 693, pp. 3-18.
Noffsinger, A.E., "Serrated Polyps and Colorectal Cancer: New Pathway to Malignancy," Annual Review of Pathology-Mechanisms of Disease, 2009, vol. 4, pp. 343-364.
O'Brien, M.J., "Hyperplastic and Serrated Polyps of the Colorectum," Gastroenterology Clinics of North America, 2007, vol. 36, pp. 947-968.
Qiu, Y., et al., "Urinary Metabonomic Study of Colorectal Cancer," Journal of Proteome Research, 2010, vol. 9, pp. 1627-1634.
Sarosiek, I. et al., "Urinary Metabolites as Noninvasive Biomarkers of Gastrointestinal Diseases: A Clinical Review" World Journal of Gastrointestinal Oncology (2016) vol. 8, Issue 5, pp. 459-465.
Slupsky, C.M., et al., "Pneumococcal Pneumonia: Potential for Diagnosis through a Urinary Metabolic Profile," Journal of Proteome Research, 2009, vol. 8, No. 12, pp. 5550-5558.
Spigelman, A.D. et al., "Caffeine Phenotyping of Cytochrome P4501A2, N-Acetyltransferase, and Xanthine Oxidase in Patients with Familial Adenomatous Polyposis" Gut (1995) vol. 36, pp. 251-254.
Supporting Information for Qiu, Y. et al., "Urinary Metabonomic Study on Colorectal Cancer" Journal of Proteome Research (2010) vol. 9, pp. 1627-1637, 9 pages total.
The Human Metabolome Database (HMDB), Metabocard for Ascorbic acid (HMDB000044). [Retrieved from the Internet Dec. 15, 2016: <http://www.hmdb.ca/metabolites/hmdb00044>].
The Human Metabolome Database (HMDB) Metabocard for Trigonelline (HMDB00875). [Retrieved from the Internet Dec. 15, 2016: <http://www.hmdb.ca/metabolites/HMDB00875>].
Torlakovic, E., et al, "Morphologic Reappraisal of Serrated Colorectal Polyps," American Journal of Surgical Pathology, 2003, vol. 27(1), pp. 65-81.
Trygg, J., "O2-PLS for qualitative and quantitative analysis in multivariate calibration," Journal of Chemometrics, 2002, vol. 16, pp. 283-293.
Trygg, J., "Prediction and spectral profile estimation in multivariate calibration," Journal of Chemometrics, 2004, vol. 18, pp. 166-172.
Deng L. et al., "Urinary Metabolomics to Identify a Unique Biomarker Panel for Detecting Colorectal Cancer: a Multicenter Study" Cancer Epidemiol Biomarkers Prev, 28(8) Aug. 2019, pp. 1283-1291.
Eriksson et al., 2013 Multi-and Megavariate Data Analysis, Basic Principles and Applications (vol. 1), Umetrics Academy, pp. 455-456.
Aguilan et al., 2020, Molecular Omics, Guide for protein fold change and p-valve calculation for non-experts in proteonomics, 16(6):573-582.
Fischer et al., Low-level maternal exposure to nicotine associates with significant metabolic pertubations in second-trimester amniotic fluid, Environ Int. 2017, 107:227-234 and supplement 7.
Du et al., Serum Metabolomics Study of Papillary Thyroid Carcinoma Based on HPLC-Q-TOF-MS/MS, Frontiers in Cell and Developmental Biology, 2021, vol. 9, Article 593510.
Margarin et al., Fetal Metabolomic Alterations Following Porcine Reproductive and Respiratory Syndrome Virus Infection, Frontiers in Molecular Biosciences, 2020, vol. 7, Article 559688.
Juang et al., The Clinical Experiences of Urine Metabolomics of Genitourinary Urothelial Cancer in a Tertiary Hospital in Taiwan, Frontiers in Oncology, 2021, vol. 11, Article 680910.
Gooding et al., LC-MS-based metabolomics analysis to identify meprin-β-associated changes in kidney tissue from mice with STZ-induced type 1 diabetes and diabetic kidney injury, Am J Physiol Renal Physiol, 2019, 317:F1034-F1046.

(56) References Cited

OTHER PUBLICATIONS

Chiu et al., Metabolomics Reveals Dynamic Metabolic Changes Associated with Age in Early Childhood, PLOS ONE, 2016, 1-14; DOI:10.1371/journal.pone.0149823.

* cited by examiner ced deaths in the world. Based on 2018 estimates,
URINARY METABOLOMIC BIOMARKERS FOR DETECTING COLORECTAL CANCER AND POLYPS

STATEMENT AS TO FEDERALLY SPONSORED RESEARCH

This invention was made with government support under grant EB024965 awarded by the National Institutes of Health. The government has certain rights in the invention.

FIELD OF THE INVENTION

This invention relates to methods and compositions for detecting colorectal cancer and colorectal polyps by measurement of metabolites in bodily fluids such as urine, including diacetylspermine and kynurenine.

BACKGROUND

Colorectal cancer (CRC) is the third most commonly diagnosed malignancy and the fourth leading cause of cancer-related deaths in the world. Based on 2018 estimates, the 2040 incidence rates for CRC are projected to increase by 72% to 3.1 million new cases while mortality rates will increase by 82% to 1.5 million deaths (1). Mortalities due to CRC are largely preventable through regular screening and early detection using fecal-based tests and colonoscopy (2). To be effective, population-based screening must be programmatic rather than opportunistic to ensure a high rate of compliance (3). Such programs have been instituted nationally or regionally within many countries in Europe (e.g., UK, Ireland, Germany, France), United States, Japan, and Australia as reviewed by Navarro and colleagues (4).

The most commonly used population-based screening modalities are the fecal immunochemical test (FIT) and colonoscopy (5). FIT detects hidden blood in stool which occurs mostly in the later stages of cancer and has low sensitivity for detecting the precursors to CRC, adenomatous polyps (9). A new fecal DNA test detects DNA mutations in addition to hidden blood in stool with improved sensitivity (6), but it is costly and only available in a few countries. To date, fecal-based tests are limited to CRC detection not prevention, and have low adherence rates due to the need for stool collection and manipulation (7-11). Colonoscopy has a superior sensitivity and specificity to non-invasive screening tests, but is costly in terms of direct and indirect health care dollars, has a higher risk of procedural-related complications, and, like fecal-based tests, has low rates of screening compliance (12).

To increase screening compliance rates, programs have largely focused on CRC education and sending reminders to eligible participants (13,14). An alternative approach for improving CRC screening rates is to use a biosample other than stool (15). A blood-based screening test has been shown to have higher patient uptake than FIT (16), but its cost-effectiveness is debatable for population-based screening (17).

SUMMARY

As specified in the Background section, above, there is a need in the art to develop improved methods for detecting colorectal cancer (CRC) and colorectal polyps. The present invention addresses these and other needs by providing methods and compositions for measurement of specific metabolites in bodily fluids.

Specifically, in the first aspect, the invention provides a method for determining the presence of colorectal cancer and/or colorectal polyps in a subject, said method comprising:
(a) obtaining a first metabolite profile from a first bodily fluid sample collected from the subject, wherein said first metabolite profile is obtained by measuring the level of each metabolite within the metabolite profile in the sample, and wherein the metabolite profile comprises diacetylspermine and/or kynurenine;
(b) comparing said first metabolite profile with a reference metabolite profile; and
(c) (i) determining the presence of colorectal cancer and/or colorectal polyps in the subject if the level of diacetylspermine and/or the level of kynurenine is increased at least 2-fold as compared to the corresponding level(s) in the reference metabolite profile, or (ii) determining that there is no colorectal cancer and/or colorectal polyps in the subject if the level of diacetylspermine and the level of kynurenine is not increased at least 2-fold as compared to the corresponding levels in the reference metabolite profile.

In some embodiments of the above method, the metabolite profile comprises diacetylspermine and kynurenine and step (c) comprises (i) determining the presence of colorectal cancer and/or colorectal polyps in the subject if the levels of diacetylspermine and kynurenine are increased at least 2-fold as compared to the corresponding levels in the reference metabolite profile, or (ii) determining that there is no colorectal cancer and/or colorectal polyps in the subject if the level of diacetylspermine or the level of kynurenine is not increased at least 2-fold as compared to the corresponding levels in the reference metabolite profile.

In some embodiments, the metabolite profile further comprises proline and/or glucose and step (c)(i) further comprises determining the presence of colorectal cancer and/or colorectal polyps in the subject if the level of proline is increased at least 2-fold and/or the level of glucose is increased at least 2-fold as compared to the corresponding level(s) in the reference metabolite profile. In some embodiments, the metabolite profile further comprises proline and glucose and step (c)(i) further comprises determining the presence of colorectal cancer and/or colorectal polyps in the subject if the level of proline is increased at least 2-fold and the level of glucose is increased at least 2-fold as compared to the corresponding levels in the reference metabolite profile.

In some embodiments, the metabolite profile further comprises one or more metabolites selected from tetradecenoyl carnitine (C14:1), 3-(3-Hydroxyphenyl)-3-hydroxypropanoic acid (HPHPA), aspartic acid, beta-hydroxybutyric acid, 3,4-dihydroxyl phenylalanine (DOPA), 4-hydroxyproline, aminoadipic acid, putrescine, indole acetic acid, hippuric acid, citric acid, sarcosine, and butyric acid. In some embodiments, the metabolite profile further comprises one or more metabolites selected from tetradecenoyl carnitine (C14:1), beta-hydroxybutyric acid, 3,4-dihydroxyl phenylalanine (DOPA), 4-hydroxyproline, putrescine, citric acid, and sarcosine and step (c)(i) further comprises determining the presence of colorectal cancer and/or colorectal polyps in the subject if the level of said one or more metabolites is increased at least 2-fold as compared to the corresponding level(s) in the reference metabolite profile. In some embodiments, the metabolite profile further comprises one or more metabolites selected from 3-(3-Hydroxyphenyl)-3-hydroxypropanoic acid (HPHPA), aspartic acid, aminoadipic acid, indole acetic acid, hippuric acid, and butyric acid and step (c)(i) further comprises determining the presence of colorectal cancer and/or colorectal polyps in the subject if the level of said one or more metabolites is decreased at least 2-fold as compared to the corresponding level(s) in the reference metabolite profile.

In some embodiments, the metabolite profile further comprises one or more metabolites selected from 1,6-anhydro-β-d-glucose, 1-methylnicotinamide, 2-hydroxyisobutyrate, 2-oxoglutarate, 3-aminoisobutyrate, 3-hydroxybutyrate, 3-hydroxyisovalerate, 3-hydroxymandelate, 3-hydroxyphenylacetate, 3-indoxylsulfate, 4-hydroxyphenylacetate, acetate, acetone, adipate, alanine, ascorbate, asparagine, benzoate, betaine, carnitine, creatine, creatinine, dimethylamine, ethanol, formate, galactose, glutamine, glycerol, glycine, glycolate, guanidoacetate, histidine, hypoxanthine, isoleucine, lactate, leucine, lysine, mannitol, methanol, methylguanidine, n,n-dimethylglycine, o-acetylcarnitine, pantothenate, propylene glycol, pyroglutamate, pyruvate, serine, succinate, sucrose, tartrate, taurine, threonine, trigonelline, trimethylamine, trimethylamine n-oxide, tyrosine, uracil, urea, valine, xylose, cis-aconitate, β-alanine, p-methylhistidine, t-methylhistidine, and trans-aconitate.

In some embodiments, the reference metabolite profile is obtained from similarly processed bodily fluid samples of healthy subjects which do not have CRC and colorectal polyps. In some embodiments, the reference metabolite profile is obtained from healthy subjects which do not have CRC and colorectal polyps as determined by colonoscopy. In one specific embodiment, the reference metabolite profile is obtained from healthy subjects which are matched to the subject being tested by age and/or gender.

In some embodiments, step (b) involves the use of one or more methods selected from a multivariate statistical analysis, logistic regression, principal component analysis (PCA), partial least squares discriminant analysis (PLS-DA), sparse PLS-DA (sPLS-DA), orthogonal partial least squares discriminant analysis (oPLS-DA), support vector machines (SVM), discriminant analysis, kernel methods, nonparametric methods, tree-based methods, generalized linear models, generalized additive modes, fuzzy logic based methods, neural networks, and genetic algorithm-based methods.

In some embodiments, the subject does not have symptoms of colorectal cancer and/or colorectal polyps.

In some embodiments, the method further comprises administering to the subject one or more additional diagnostic tests selected from fecal occult blood test (FOBT), fecal immunochemical test (FIT), fecal DNA tests, flexible sigmoidoscopy, blood septin 9 tests, air-contrast barium enema, computed tomography colonography (CTC), and colonoscopy. In some embodiments, the method further comprises administering to the subject a colonoscopy. In some embodiments, the method further comprises administering to the subject a fecal DNA test to identify mutations in KRAS and/or TP53 and/or APC genes.

In some embodiments, the method further comprises enrolling the subject in a clinical trial.

In some embodiments, the method further comprises administering to the subject one or more treatments for CRC and/or colorectal polyps. Non-limiting examples of useful treatments comprise, for example, a surgical removal of CRC tumor and/or colorectal polyp, a radiation therapy, administering one or more pharmacological agents (e.g., oxaliplatin, irinotecan, capecitabine, tegafur, leucovorin, trifluridine, tipiracil hydrochloride, lanreotide acetate, arfolitixorin, 5-fluorouracil, raltitrexed, antibodies [e.g., bevacizumab, cetuximab, ipilimumab, monalizumab, oleclumab, panitumumab, ramacurimab, and biosimilars thereof], immune checkpoint inhibitors [e.g., avelumab, atezolizumab, camrelizumab, durvalumab, nivolumab, pembrolizumab, pidilizumab, and biosimilars thereof], inhibitors with antineoplastic activities [e.g., BRAF inhibitors, MEK inhibitors, TGF beta inhibitors, Akt/ERK inhibitors, tyrosine kinase inhibitors, and pemigatinib], antineoplastic agents with antiretroviral or immunomodulatory activities, and any combinations thereof.

In a related aspect, the invention provides a method for treating colorectal cancer and/or colorectal polyps in a subject, said method comprising:
(a) obtaining a first metabolite profile from a first bodily fluid sample collected from the subject, wherein said first metabolite profile is obtained by measuring the level of each metabolite within the metabolite profile in the sample, wherein the metabolite profile comprises diacetylspermine and/or kynurenine;
(b) comparing said first metabolite profile with a reference metabolite profile; and
(c) determining the presence of colorectal cancer and/or colorectal polyps in the subject if the level of diacetylspermine and/or the level of kynurenine is increased at least 2-fold as compared to the corresponding level(s) in the reference metabolite profile, and
(d) administering to the subject one or more treatments for CRC and/or colorectal polyps.

In some embodiments of the above treatment method, the metabolite profile comprises diacetylspermine and kynurenine and step (c) comprises determining the presence of colorectal cancer and/or colorectal polyps in the subject if the levels of diacetylspermine and kynurenine are increased at least 2-fold as compared to the corresponding levels in the reference metabolite profile.

In some embodiments of the above treatment method, the metabolite profile further comprises proline and/or glucose and step (c) further comprises determining the presence of colorectal cancer and/or colorectal polyps in the subject if the level of proline is increased at least 2-fold and/or the level of glucose is increased at least 2-fold as compared to the corresponding level(s) in the reference metabolite profile. In some embodiments, the metabolite profile further comprises proline and glucose and step (c) further comprises determining the presence of colorectal cancer and/or colorectal polyps in the subject if the level of proline is increased at least 2-fold and the level of glucose is increased at least 2-fold as compared to the corresponding levels in the reference metabolite profile.

In some embodiments of the above treatment method, the metabolite profile further comprises one or more metabolites selected from tetradecenoyl carnitine (C14:1), 3-(3-Hydroxyphenyl)-3-hydroxypropanoic acid (HPHPA), aspartic acid, beta-hydroxybutyric acid, 3,4-dihydroxyl phenylalanine (DOPA), 4-hydroxyproline, aminoadipic acid, putrescine, indole acetic acid, hippuric acid, citric acid, sarcosine, and butyric acid. In some embodiments, the metabolite profile further comprises one or more metabolites selected from tetradecenoyl carnitine (C14:1), beta-hydroxybutyric acid, 3,4-dihydroxyl phenylalanine (DOPA), 4-hydroxyproline, putrescine, citric acid, and sarcosine and step (c) further comprises determining the presence of colorectal cancer and/or colorectal polyps in the subject if the level of said one or more metabolites is increased at least 2-fold as compared to the corresponding level(s) in the reference metabolite profile. In some embodiments, the metabolite profile further comprises one or more metabolites selected from 3-(3-Hydroxyphenyl)-3-hydroxypropanoic acid (HPHPA), aspartic acid, aminoadipic acid, indole acetic acid, hippuric acid, and butyric acid and step (c) further comprises determining the presence of colorectal cancer and/or colorectal polyps in the subject if the level of said one or more metabolites is decreased at least 2-fold as compared to the corresponding level(s) in the reference metabolite profile.

In some embodiments of the above treatment method, the metabolite profile further comprises one or more metabolites selected from 1,6-anhydro-β-d-glucose, 1-methylnicotinamide, 2-hydroxyisobutyrate, 2-oxoglutarate, 3-aminoisobutyrate, 3-hydroxybutyrate, 3-hydroxyisovalerate, 3-hydroxymandelate, 3-hydroxyphenylacetate, 3-indoxylsulfate, 4-hydroxyphenylacetate, acetate, acetone, adipate, alanine, ascorbate, asparagine, benzoate, betaine, carnitine, creatine, creatinine, dimethylamine, ethanol, formate, galactose, glutamine, glycerol, glycine, glycolate, guanidoacetate, histidine, hypoxanthine, isoleucine, lactate, leucine, lysine, mannitol, methanol, methylguanidine, n,n-dimethylglycine, o-acetylcarnitine, pantothenate, propylene glycol, pyroglutamate, pyruvate, serine, succinate, sucrose, tartrate, taurine, threonine, trigonelline, trimethylamine, trimethylamine n-oxide, tyrosine, uracil, urea, valine, xylose, cis-aconitate, β-alanine, p-methylhistidine, t-methylhistidine, and trans-aconitate.

In some embodiments of the above treatment method, the reference metabolite profile is obtained from similarly processed bodily fluid samples of healthy subjects which do not have CRC and colorectal polyps. In some embodiments, said reference metabolite profile is obtained from healthy subjects which do not have CRC and colorectal polyps as determined by colonoscopy. In some embodiments, said reference metabolite profile is obtained from healthy subjects which are matched to the subject being tested by age and/or gender.

In some embodiments of the above treatment method, step (b) involves the use of one or more methods selected from a multivariate statistical analysis, logistic regression, principal component analysis (PCA), partial least squares discriminant analysis (PLS-DA), sparse PLS-DA (sPLS-DA), orthogonal partial least squares discriminant analysis (oPLS-DA), support vector machines (SVM), discriminant analysis, kernel methods, nonparametric methods, tree-based methods, generalized linear models, generalized additive modes, fuzzy logic based methods, neural networks, and genetic algorithm-based methods.

In some embodiments of the above treatment method, the subject does not have symptoms of colorectal cancer and/or colorectal polyps.

In some embodiments of the above treatment method, the method further comprises administering to the subject one or more additional diagnostic tests selected from fecal occult blood test (FOBT), fecal immunochemical test (FIT), fecal DNA tests, flexible sigmoidoscopy, blood septin 9 tests, air-contrast barium enema, computed tomography colonography (CTC), and colonoscopy. In some embodiments, the method further comprises administering to the subject a colonoscopy. In some embodiments, the method further comprises administering to the subject a fecal DNA test to identify mutations in KRAS and/or TP53 and/or APC genes.

In some embodiments of the above treatment method, the treatment comprises a surgical removal of CRC tumor and/or colorectal polyp. In some embodiments, the treatment comprises a radiation therapy. In some embodiments, the treatment comprises administering one or more pharmacological agents. Non-limiting examples of useful pharmacological agents comprise, for example, oxaliplatin, irinotecan, capecitabine, tegafur, leucovorin, trifluridine, tipiracil hydrochloride, lanreotide acetate, arfolitixorin, 5-fluorouracil, raltitrexed, antibodies (e.g., bevacizumab, cetuximab, ipilimumab, monalizumab, oleclumab, panitumumab, ramacurimab, and biosimilars thereof), immune checkpoint inhibitors (e.g., avelumab, atezolizumab, camrelizumab, durvalumab, nivolumab, pembrolizumab, pidilizumab, and biosimilars thereof), inhibitors with antineoplastic activities (e.g., BRAF inhibitors, MEK inhibitors, TGF beta inhibitors, Akt/ERK inhibitors, tyrosine kinase inhibitors, and pemigatinib), antineoplastic agents with antiretroviral or immunomodulatory activities, and any combinations thereof.

In a related aspect, the invention provides a method for monitoring the progression of colorectal cancer and/or colorectal polyps in a subject diagnosed with colorectal cancer and/or colorectal polyps, said method comprising:

(a) obtaining metabolite profiles in two or more bodily fluid samples collected from the subject at spaced apart time points, wherein said metabolite profiles are obtained by measuring the level of each metabolite within the metabolite profile in the sample and wherein said metabolite profiles comprise diacetylspermine and/or kynurenine;

(b) comparing metabolite profiles between earlier collected and later collected bodily fluid samples; and (c) (i) determining that the colorectal cancer and/or colorectal polyps in the subject have progressed if the level of diacetylspermine and/or the level of kynurenine is increased at least 2-fold in the later collected bodily fluid sample(s) as compared to the earlier collected bodily fluid sample(s), or (ii) determining that the colorectal cancer and/or colorectal polyps in the subject have not progressed if the level of diacetylspermine and the level of kynurenine is not increased in the later collected bodily fluid sample(s) as compared to the earlier collected bodily fluid sample(s).

In some embodiments of the above progression monitoring method, the metabolite profiles comprise diacetylspermine and kynurenine and step (c) comprises (i) determining that the colorectal cancer and/or colorectal polyps in the subject have progressed if the levels of diacetylspermine and kynurenine are increased at least 2-fold in the later collected bodily fluid sample(s) as compared to the earlier collected bodily fluid sample(s), or (ii) determining that the colorectal cancer and/or colorectal polyps in the subject have not progressed if the level of diacetylspermine or the level of kynurenine is not increased in the later collected bodily fluid sample(s) as compared to the earlier collected bodily fluid sample(s).

In some embodiments of the above progression monitoring method, the bodily fluid samples are collected from the subject 3 or more months apart.

In some embodiments of the above progression monitoring method, the metabolite profile further comprises proline and/or glucose and step (c)(i) further comprises determining that the colorectal cancer and/or colorectal polyps in the subject have progressed if the level of proline is increased at least 2-fold and/or the level of glucose is increased at least 2-fold in the later collected bodily fluid sample(s) as compared to the earlier collected bodily fluid sample(s). In some embodiments, the metabolite profile further comprises proline and glucose and step (c)(i) further comprises determining that the colorectal cancer and/or colorectal polyps in the subject have progressed if the level of proline is increased at least 2-fold and the level of glucose is increased at least 2-fold in the later collected bodily fluid sample(s) as compared to the earlier collected bodily fluid sample(s).

In some embodiments of the above progression monitoring method, the metabolite profile further comprises one or more metabolites selected from tetradecenoyl carnitine (C14:1), 3-(3-Hydroxyphenyl)-3-hydroxypropanoic acid (HPHPA), aspartic acid, beta-hydroxybutyric acid, 3,4-dihydroxyl phenylalanine (DOPA), 4-hydroxyproline, aminoadipic acid, putrescine, indole acetic acid, hippuric acid, citric acid, sarcosine, and butyric acid. In some embodiments, the metabolite profile further comprises one or more metabolites selected from tetradecenoyl carnitine (C14:1), beta-hydroxybutyric acid, 3,4-dihydroxyl phenylalanine (DOPA), 4-hydroxyproline, putrescine, citric acid, and sarcosine and step (c)(i) further comprises determining that the colorectal cancer and/or colorectal polyps in the subject have progressed if the level of said one or more metabolites is increased at least 2-fold in the later collected bodily fluid sample(s) as compared to the earlier collected bodily fluid sample(s). In some embodiments, the metabolite profile further comprises one or more metabolites selected from 3-(3-Hydroxyphenyl)-3-hydroxypropanoic acid (HPHPA), aspartic acid, aminoadipic acid, indole acetic acid, hippuric acid, and butyric acid and step (c)(i) further comprises determining that the colorectal cancer and/or colorectal polyps in the subject have progressed if the level of said one or more metabolites is decreased at least 2-fold in the later collected bodily fluid sample(s) as compared to the earlier collected bodily fluid sample(s).

In some embodiments of the above progression monitoring method, the metabolite profile further comprises one or more metabolites selected from 1,6-anhydro-β-d-glucose, 1-methylnicotinamide, 2-hydroxyisobutyrate, 2-oxoglutarate, 3-aminoisobutyrate, 3-hydroxybutyrate, 3-hydroxyisovalerate, 3-hydroxymandelate, 3-hydroxyphenylacetate, 3-indoxylsulfate, 4-hydroxyphenylacetate, acetate, acetone, adipate, alanine, ascorbate, asparagine, benzoate, betaine, carnitine, creatine, creatinine, dimethylamine, ethanol, formate, galactose, glutamine, glycerol, glycine, glycolate, guanidoacetate, histidine, hypoxanthine, isoleucine, lactate, leucine, lysine, mannitol, methanol, methylguanidine, n,n-dimethylglycine, o-acetylcarnitine, pantothenate, propylene glycol, pyroglutamate, pyruvate, serine, succinate, sucrose, tartrate, taurine, threonine, trigonelline, trimethylamine, trimethylamine n-oxide, tyrosine, uracil, urea, valine, xylose, cis-aconitate, β-alanine, p-methylhistidine, t-methylhistidine, and trans-aconitate.

In some embodiments of the above progression monitoring method, step (b) involves the use of one or more methods selected from a multivariate statistical analysis, logistic regression, principal component analysis (PCA), partial least squares discriminant analysis (PLS-DA), sparse PLS-DA (sPLS-DA), orthogonal partial least squares discriminant analysis (oPLS-DA), support vector machines (SVM), discriminant analysis, kernel methods, nonparametric methods, tree-based methods, generalized linear models, generalized additive modes, fuzzy logic based methods, neural networks, and genetic algorithm-based methods.

In some embodiments of the above progression monitoring method, the method further comprises enrolling the subject in a clinical trial.

In some embodiments of the above progression monitoring method, the method further comprises administering to the subject one or more treatments for CRC and/or colorectal polyps. Non-limiting examples of useful treatments comprise, for example, a surgical removal of CRC tumor and/or colorectal polyp, a radiation therapy, administering one or more pharmacological agents (e.g., oxaliplatin, irinotecan, capecitabine, tegafur, leucovorin, trifluridine, tipiracil hydrochloride, lanreotide acetate, arfolitixorin, 5-fluorouracil, raltitrexed, antibodies [e.g., bevacizumab, cetuximab, ipilimumab, monalizumab, oleclumab, panitumumab, ramacurimab, and biosimilars thereof], immune checkpoint inhibitors [e.g., avelumab, atezolizumab, camrelizumab, durvalumab, nivolumab, pembrolizumab, pidilizumab, and biosimilars thereof], inhibitors with antineoplastic activities [e.g., BRAF inhibitors, MEK inhibitors, TGF beta inhibitors, Akt/ERK inhibitors, tyrosine kinase inhibitors, and pemigatinib], antineoplastic agents with antiretroviral or immunomodulatory activities, and any combinations thereof.

In a further related aspect, the invention provides a method for determining the effect of a treatment on development of colorectal cancer and/or colorectal polyps in a subject diagnosed with colorectal cancer and/or colorectal polyps, said method comprising:
  (a) obtaining metabolite profiles in bodily fluid samples collected from the subject prior to and after administering the treatment, wherein said metabolite profiles are obtained by measuring the level of each metabolite within the metabolite profile in the sample and wherein said metabolite profiles comprise diacetylspermine and/or kynurenine;
  (b) comparing metabolite profiles between the bodily fluid samples collected from the subject prior to and after administering the treatment; and
  (c) (i) determining that the treatment is effective if the level of diacetylspermine and the level of kynurenine is not increased at least 2-fold in the bodily fluid sample(s) collected after administering the treatment as compared to the bodily fluid sample(s) collected before administering the treatment, or (ii) determining that the treatment is not effective if the level of diacetylspermine and/or the level of kynurenine is increased at least 2-fold in the bodily fluid sample(s) collected after administering the treatment as compared to the bodily fluid sample(s) collected before administering the treatment.

In some embodiments of the above method for determining the effect of a treatment, the metabolite profiles comprise diacetylspermine and kynurenine and step (c) comprises (i) determining that the treatment is effective if the levels of diacetylspermine and kynurenine are not increased at least 2-fold in the bodily fluid sample(s) collected after administering the treatment as compared to the bodily fluid sample(s) collected before administering the treatment, or (ii) determining that the treatment is not effective if the level of diacetylspermine or the level of kynurenine is increased at least 2-fold in the bodily fluid sample(s) collected after administering the treatment as compared to the bodily fluid sample(s) collected before administering the treatment.

In some embodiments of the above method for determining the effect of a treatment, the method comprises prior to step (a) the following steps:
  (1) collecting one or more bodily fluid sample(s) from the subject prior to initiation of the treatment,
  (2) administering the treatment to the subject, and
  (3) collecting one or more bodily fluid sample(s) from the subject in the course of or following the treatment.

In some embodiments of the above method for determining the effect of a treatment, the metabolite profile further comprises proline and/or glucose and step (c)(i) further comprises determining that the treatment is effective if the level of proline and/or the level of glucose is not increased at least 2-fold in the bodily fluid sample(s) collected after administering the treatment as compared to the bodily fluid sample(s) collected before administering the treatment. In some embodiments, the metabolite profile further comprises proline and glucose and step (c)(i) further comprises determining that the treatment is effective if the level of proline and the level of glucose is not increased at least 2-fold in the bodily fluid sample(s) collected after administering the treatment as compared to the bodily fluid sample(s) collected before administering the treatment.

In some embodiments of the above method for determining the effect of a treatment, the metabolite profile further comprises one or more metabolites selected from tetradecenoyl carnitine (C14:1), 3-(3-Hydroxyphenyl)-3-hydroxypropanoic acid (HPHPA), aspartic acid, beta-hydroxybutyric acid, 3,4-dihydroxyl phenylalanine (DOPA), 4-hydroxyproline, aminoadipic acid, putrescine, indole acetic acid, hippuric acid, citric acid, sarcosine, and butyric acid. In some embodiments, the metabolite profile further comprises one or more metabolites selected from tetradecenoyl carnitine (C14:1), beta-hydroxybutyric acid, 3,4-dihydroxyl phenylalanine (DOPA), 4-hydroxyproline, putrescine, citric acid, and sarcosine and step (c)(i) further comprises determining that the treatment is effective if the level of said one or more metabolites is not increased at least 2-fold in the bodily fluid sample(s) collected after administering the treatment as compared to the bodily fluid sample(s) collected before administering the treatment. In some embodiments, the metabolite profile further comprises one or more metabolites selected from 3-(3-Hydroxyphenyl)-3-hydroxypropanoic acid (HPHPA), aspartic acid, aminoadipic acid, indole acetic acid, hippuric acid, and butyric acid and step (c)(i) further comprises determining that the treatment is effective if the level of said one or more metabolites is increased at least 2-fold in the bodily fluid sample(s) collected after administering the treatment as compared to the bodily fluid sample(s) collected before administering the treatment.

In some embodiments of the above method for determining the effect of a treatment, the metabolite profile further comprises one or more metabolites selected from 1,6-anhydro-β-d-glucose, 1-methylnicotinamide, 2-hydroxyisobutyrate, 2-oxoglutarate, 3-aminoisobutyrate, 3-hydroxybutyrate, 3-hydroxyisovalerate, 3-hydroxymandelate, 3-hydroxyphenylacetate, 3-indoxylsulfate, 4-hydroxyphenylacetate, acetate, acetone, adipate, alanine, ascorbate, asparagine, benzoate, betaine, carnitine, creatine, creatinine, dimethylamine, ethanol, formate, galactose, glutamine, glycerol, glycine, glycolate, guanidoacetate, histidine, hypoxanthine, isoleucine, lactate, leucine, lysine, mannitol, methanol, methylguanidine, n,n-dimethylglycine, o-acetylcarnitine, pantothenate, propylene glycol, pyroglutamate, pyruvate, serine, succinate, sucrose, tartrate, taurine, threonine, trigonelline, trimethylamine, trimethylamine n-oxide, tyrosine, uracil, urea, valine, xylose, cis-aconitate, β-alanine, p-methylhistidine, t-methylhistidine, and trans-aconitate.

In some embodiments of the above method for determining the effect of a treatment, step (b) involves the use of one or more methods selected from a multivariate statistical analysis, logistic regression, principal component analysis (PCA), partial least squares discriminant analysis (PLS-DA), sparse PLS-DA (sPLS-DA), orthogonal partial least squares discriminant analysis (oPLS-DA), support vector machines (SVM), discriminant analysis, kernel methods, nonparametric methods, tree-based methods, generalized linear models, generalized additive modes, fuzzy logic based methods, neural networks, and genetic algorithm-based methods.

In another related aspect, the invention provides a method for identifying a compound useful for slowing down the progression or treating colorectal cancer and/or colorectal polyps in a subject diagnosed with colorectal cancer and/or colorectal polyps, said method comprising:
(a) obtaining metabolite profiles in bodily fluid samples collected from the subject prior to and after administering a test compound, wherein said metabolite profiles are obtained by measuring the level of each metabolite within the metabolite profile in the sample and wherein said metabolite profiles comprise diacetylspermine and/or kynurenine;
(b) comparing metabolite profiles between the bodily fluid samples collected from the subject prior to and after administering the test compound; and
(c) (i) determining that the test compound is effective for slowing down the progression or treating colorectal cancer and/or colorectal polyps if the level of diacetylspermine and kynurenine is not increased in the bodily fluid sample(s) collected after administering the test compound as compared to the bodily fluid sample(s) collected before administering the test compound, or (ii) determining that the test compound is not effective for slowing down the progression or treating colorectal cancer and/or colorectal polyps if the level of diacetylspermine and/or kynurenine is increased at least 2-fold in the bodily fluid sample(s) collected after administering the test compound as compared to the bodily fluid sample(s) collected before administering the test compound.

In some embodiments of the above method for identifying a compound useful for slowing down the progression or treating CRC and/or colorectal polyps, the metabolite profiles comprise diacetylspermine and kynurenine and step (c) comprises (i) determining that the test compound is effective for slowing down the progression or treating colorectal cancer and/or colorectal polyps if the levels of diacetylspermine and kynurenine are not increased in the bodily fluid sample(s) collected after administering the test compound as compared to the bodily fluid sample(s) collected before administering the test compound, or (ii) determining that the test compound is not effective for slowing down the progression or treating colorectal cancer and/or colorectal polyps if the levels of diacetylspermine and/or kynurenine are increased at least 2-fold in the bodily fluid sample(s) collected after administering the test compound as compared to the bodily fluid sample(s) collected before administering the test compound.

In some embodiments of the above method for identifying a compound useful for slowing down the progression or treating CRC and/or colorectal polyps, the method comprises prior to step (a) the following steps:
(1) collecting one or more bodily fluid sample(s) from the subject prior to administering the test compound,
(2) administering the test compound to the subject, and
(3) collecting one or more bodily fluid sample(s) from the subject after administering the test compound.

In some embodiments of the above method for identifying a compound useful for slowing down the progression or treating CRC and/or colorectal polyps, the metabolite profile further comprises proline and/or glucose and step (c)(i) further comprises determining that the test compound is effective for slowing down the progression or treating colorectal cancer and/or colorectal polyps if the level of proline and/or the level of glucose is not increased at least 2-fold in the bodily fluid sample(s) collected after administering the test compound as compared to the bodily fluid sample(s)

collected before administering the test compound. In some embodiments, the metabolite profile further comprises proline and glucose and step (c)(i) further comprises determining that the test compound is effective for slowing down the progression or treating colorectal cancer and/or colorectal polyps if the level of proline and the level of glucose is not increased at least 2-fold in the bodily fluid sample(s) collected after administering the test compound as compared to the bodily fluid sample(s) collected before administering the test compound.

In some embodiments of the above method for identifying a compound useful for slowing down the progression or treating CRC and/or colorectal polyps, the metabolite profile further comprises one or more metabolites selected from tetradecenoyl carnitine (C14:1), 3-(3-Hydroxyphenyl)-3-hydroxypropanoic acid (HPHPA), aspartic acid, beta-hydroxybutyric acid, 3,4-dihydroxyl phenylalanine (DOPA), 4-hydroxyproline, aminoadipic acid, putrescine, indole acetic acid, hippuric acid, citric acid, sarcosine, and butyric acid. In some embodiments, the metabolite profile further comprises one or more metabolites selected from tetradecenoyl carnitine (C14:1), beta-hydroxybutyric acid, 3,4-dihydroxyl phenylalanine (DOPA), 4-hydroxyproline, putrescine, citric acid, and sarcosine and step (c)(i) further comprises determining that the treatment is effective if the level of said one or more metabolites is not increased at least 2-fold in the bodily fluid sample(s) collected after administering the test compound as compared to the bodily fluid sample(s) collected before administering the test compound. In some embodiments, the metabolite profile further comprises one or more metabolites selected from 3-(3-Hydroxyphenyl)-3-hydroxypropanoic acid (HPHPA), aspartic acid, aminoadipic acid, indole acetic acid, hippuric acid, and butyric acid and step (c)(i) further comprises determining that the test compound is effective for slowing down the progression or treating colorectal cancer and/or colorectal polyps if the level of said one or more metabolites is increased at least 2-fold in the bodily fluid sample(s) collected after administering the test compound as compared to the bodily fluid sample(s) collected before administering the test compound.

In some embodiments of the above method for identifying a compound useful for slowing down the progression or treating CRC and/or colorectal polyps, the metabolite profile further comprises one or more metabolites selected from 1,6-anhydro-β-d-glucose, 1-methylnicotinamide, 2-hydroxyisobutyrate, 2-oxoglutarate, 3-aminoisobutyrate, 3-hydroxybutyrate, 3-hydroxyisovalerate, 3-hydroxymandelate, 3-hydroxyphenylacetate, 3-indoxylsulfate, 4-hydroxyphenylacetate, acetate, acetone, adipate, alanine, ascorbate, asparagine, benzoate, betaine, carnitine, creatine, creatinine, dimethylamine, ethanol, formate, galactose, glutamine, glycerol, glycine, glycolate, guanidoacetate, histidine, hypoxanthine, isoleucine, lactate, leucine, lysine, mannitol, methanol, methylguanidine, n,n-dimethylglycine, o-acetylcarnitine, pantothenate, propylene glycol, pyroglutamate, pyruvate, serine, succinate, sucrose, tartrate, taurine, threonine, trigonelline, trimethylamine, trimethylamine n-oxide, tyrosine, uracil, urea, valine, xylose, cis-aconitate, β-alanine, p-methylhistidine, t-methylhistidine, and trans-aconitate.

In some embodiments of the above method for identifying a compound useful for slowing down the progression or treating CRC and/or colorectal polyps, step (b) involves the use of one or more methods selected from a multivariate statistical analysis, logistic regression, principal component analysis (PCA), partial least squares discriminant analysis (PLS-DA), sparse PLS-DA (sPLS-DA), orthogonal partial least squares discriminant analysis (oPLS-DA), support vector machines (SVM), discriminant analysis, kernel methods, nonparametric methods, tree-based methods, generalized linear models, generalized additive modes, fuzzy logic based methods, neural networks, and genetic algorithm-based methods.

In some embodiments of any of the above methods of the invention, prior to measuring metabolite levels, the bodily fluid sample(s) is refrigerated, frozen, dried, treated by administering an anti-bacterial agent, treated by administering an antifungal agent, or any combination thereof.

In some embodiments of any of the above methods of the invention, the levels of the metabolites are measured using one or more methods selected from nuclear magnetic resonance (NMR) spectroscopy, liquid chromatography-mass spectrometry (LC-MS), reverse-phase liquid chromatography-mass spectrometry (LC-MS), direct injection mass spectrometry, high performance liquid chromatography (HPLC), gas chromatography, thin layer chromatography, electrochemical analysis, mass spectroscopy, refractive index spectroscopy, ultra-violet spectroscopy, fluorescent analysis, radiochemical analysis, near-infrared spectroscopy, gas chromatography, impedance analysis, colorimetric analysis, and light scattering analysis.

In some embodiments of any of the above methods of the invention, the subject is human. In some embodiments, the subject is an experimental or a veterinary animal.

In another aspect, the invention provides a kit (i) for determining the presence of colorectal cancer and/or colorectal polyps in a subject or (ii) for determining the progression of colorectal cancer and/or colorectal polyps in a subject diagnosed with colorectal cancer and/or colorectal polyps or (iii) for determining the effect of a treatment on development of colorectal cancer and/or colorectal polyps in a subject diagnosed with colorectal cancer and/or colorectal polyps or (iv) for identifying a compound useful for slowing down the progression or treating colorectal cancer and/or colorectal polyps in a subject diagnosed with colorectal cancer and/or colorectal polyps, said kit comprising:

(a) one or more reagents for detecting in a bodily fluid sample the level of one or more metabolites selected from diacetylspermine, proline, tetradecenoyl carnitine (C14:1), kynurenine, glucose, 3-(3-Hydroxyphenyl)-3-hydroxypropanoic acid (HPHPA), aspartic acid, beta-hydroxybutyric acid, 3,4-dihydroxyl phenylalanine (DOPA), 4-hydroxyproline, aminoadipic acid, putrescine, indole acetic acid, hippuric acid, citric acid, sarcosine, and butyric acid,
  (b) optionally, one or more reagents for purifying and/or treating the bodily fluid sample, and
  (c) optionally, instructions for use.

In a further aspect, the invention provides a use of a metabolite profile comprising diacetylspermine and/or kynurenine (i) for determining the presence of colorectal cancer and/or colorectal polyps in a subject or (ii) for determining the progression of colorectal cancer and/or colorectal polyps in a subject diagnosed with colorectal cancer and/or colorectal polyps or (iii) for determining the effect of a treatment on development of colorectal cancer and/or colorectal polyps in a subject diagnosed with colorectal cancer and/or colorectal polyps or (iv) for identifying a compound useful for slowing down the progression or treating colorectal cancer and/or colorectal polyps in a subject diagnosed with colorectal cancer and/or colorectal polyps. In some embodiments, the metabolite profile comprises diacetylspermine and kynurenine. In some embodiments, the metabolite profile further comprises proline and/ or glucose. In some embodiments, the metabolite profile further comprises one or more metabolites selected from tetradecenoyl carnitine (C14:1), 3-(3-Hydroxyphenyl)-3-hydroxypropanoic acid (HPHPA), aspartic acid, beta-hydroxybutyric acid, 3,4-dihydroxyl phenylalanine (DOPA), 4-hydroxyproline, aminoadipic acid, putrescine, indole acetic acid, hippuric acid, citric acid, sarcosine, and butyric acid.

In some embodiments of any of the methods or uses of the present invention, the bodily fluid sample is selected from urine, blood, serum, and saliva. In some embodiments, the bodily fluid sample is a urine sample.

Any combinations of the above individual embodiments are also encompassed by the present application.

These and other aspects of the present invention will become apparent to those skilled in the art after a reading of the following detailed description of the invention, including the appended claims.

DETAILED DESCRIPTION

Figure 1A:
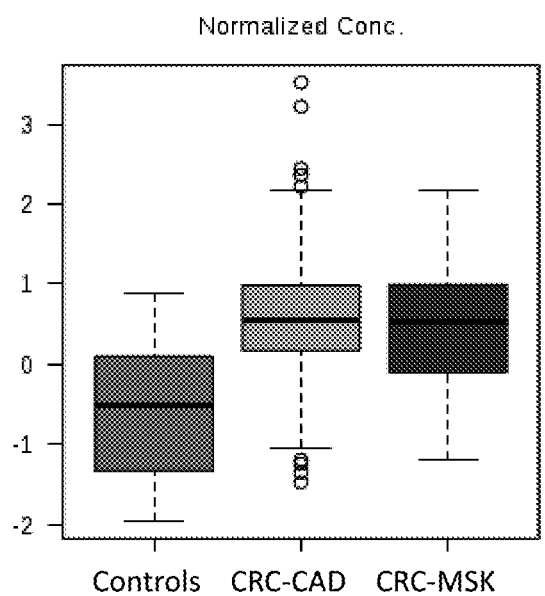
FIGS. 1A-1D show normalized levels of metabolites for controls, CRC-CAD, and CRC-MSK study groups for diacetylspermine (FIG. 1A); HPHPA (FIG. 1B); aspartic acid (FIG. 1C); and, butyric acid (FIG. 1D).

Unless defined otherwise, all technical and scientific terms used herein have the same meaning as commonly understood to one of ordinary skill in the art to which this invention belongs. As used in this specification and the appended claims, the singular forms "a," "an," and "the" include plural reference unless the context clearly dictates otherwise.

Population-based screening programs are credited with earlier colorectal cancer (CRC) diagnoses and treatment initiation which reduce mortality rates and improve patient health outcomes. However, recommended screening methods are unsatisfactory for global purposes as they are invasive, resource intensive, suffer from low uptake, or have poor diagnostic performance. Therefore, there is a need to identify a bodily fluid metabolomic-based biomarker panel for the detection of CRC that has the potential for global population-based screening.

Urine is commonly used for many clinical tests, can be readily collected, and is more acceptable to patients (18,19). Recently, putative biomarkers of CRC were identified in urine in various forms (20-26).

The inventors investigated the potential utility of urine-based metabolomics for detecting CRC and/or colorectal polyps. This was done by analyzing metabolites in urine samples from colonoscopy- and histopathology-confirmed cases of CRC and healthy controls (e.g., polyp- and CRC-free). These findings highlight the predictive potential of urinary metabolites for CRC. A screening test was developed which has clinical relevance.

As detailed in the Examples section, below, prospective urine samples were collected from study participants. Based upon colonoscopy and histopathology results, 342 participants (CRC, 171; healthy controls, 171) from two study sites (e.g., Canada, United States) were included in the analyses. Targeted liquid chromatography-mass spectrometry was performed to quantify 140 highly valuable metabolites in each urine sample. Potential biomarkers for CRC and/or colorectal polyps were identified by comparing the metabolomic profiles from CRC versus controls. Multiple models were constructed leading to a good separation of CRC from controls.

A panel of 17 metabolites was identified as possible biomarkers for CRC and/or colorectal polyps. Using only two of the selected metabolites, namely (i.e., diacetylspermine and kynurenine), a predictor for the detection of CRC and/or colorectal polyps was built with an AUC of 0.864, a specificity of 80.0% and a sensitivity of 80.0%.

CRC and Colorectal Polyps

CRC is among the leading causes of morbidity. CRC is the third most common malignancy in the world and represents approximately 10% of the world's total cancer incidence. CRC appears not only in humans but also in animal species, and in both sexes. Among human beings, more than 9 out of 10 people diagnosed with CRC are over the age of 50. However, younger individuals can develop CRC.

The chance of surviving CRC is closely related to the stage of the disease at diagnosis. The likelihood of survival is greater if the diagnosis is made earlier, permitting earlier treatment. Adenomatous and some other types of colorectal polyps may progress to malignant carcinomas and may thus be indicative that a subject is at risk of developing CRC. Thus, not only is it beneficial to be able to detect CRC itself, it is useful to be able to detect also the presence of precancerous lesions such as colorectal polyps.

There are a number of types of colorectal polyps. Adenomatous polyps are known to be a precursor to full-blown CRC. Other types of polyps may not themselves have malignant potential. Nevertheless, they may be useful indicators that a subject is at risk of developing CRC. For instance, unlike adenomatous polyps, hyperplastic polyps have been historically recognized as benign growths of the colon that have no malignant potential—i.e. they were thought to be innocent bystanders. However, hyperplastic polyps have been noted to be more prevalent in populations with a higher incidence of cancer. Moreover, hyperplastic polyps may represent a heterogenous group of polyps, some of which have significant risk for malignant potential. These potentially malignant lesions are known as sessile serrated adenoma and have been linked to the microsatellite instability cancer pathway and thus are potential precursors of sporadic microsatellite unstable CRC.

Currently, the risk factors for CRC are not well understood and few specific risk factors other than diet have been established for the disease. As such, CRC is typically diagnosed from a complete subject history and physical examination, followed by endoscopic and/or radiological imaging. The diagnosis is confirmed with histopathological examination of biopsies or surgically removed specimens.

Current CRC screening methods consist of fecal occult blood test (FOBT), fecal immunochemical test (FIT), fecal DNA tests, blood septin 9 tests, flexible sigmoidoscopy, air-contrast barium enema, computed tomography colonography (CTC), and colonoscopy. See, e.g., Issa and Noureddine, World J Gastroenterol., 2017, 23(28):5086; Hamzehzadeh et al., Int J Hematol Oncol Stem Cell Res., 2017, 11(3):250-261. These current screening methods all have limitations or potential risks that limit their application.

Colonoscopy is currently the standard test for assessing the presence or absence of CRC and/or colorectal polyps. However, colonoscopy is invasive and can impose unnecessary hazards and risks to an individual caused by sedation or the procedure itself, and complications with colonoscopy can include perforation, hemorrhage, respiratory depression, arrhythmias, and infection. In addition, it requires considerable physical resources and skilled personnel.

Known non-invasive CRC diagnostic method is fecal occult blood test (FOBT) and fecal immunochemical test (FIT) which both detect hidden blood in stool (using chemical and immunological assays, respectively) which occurs mostly in the later stages of cancer and have low sensitivity for detecting the precursors to CRC, adenomatous polyps. FOBT involves a crude test for the peroxidase-like activity of heme in hemoglobin. The sensitivity of the test is only approximately 50% for CRC, with a 20% sensitivity for adenomatous polyps. In addition, FOBT and FIT are unattractive tests for subjects as the handling of fecal matter is required.

Computed tomography colonography (CTC), or virtual colonoscopy, is a recent non-invasive technique for imaging the colon. However, its performance varies due primarily to technological differences in the subject preparation and the hardware and software used for the analysis. Other limitations of CTC include high false positives (FP) readings, inability to detect flat adenomas, no capacity to remove polyps, repetitive and cumulative radiation doses, and cost.

With advances in the CRC related molecular pathology, several new screening methods based on DNA analysis from stool samples became available. These are typically PCR-based assays used to identify mutations known to occur in the adenoma-to-carcinoma sequence, or in familial CRC. Commonly screened gene mutations include KRAS, TP53, APC, as well as assays for micro satellite instability and hypermethylated DNA. However, whether genomics-based tests will result in high diagnostic accuracy for sporadic CRC remains to be seen.

Metabolomics and Diagnosis of CRC or Colorectal Polyps

Metabolomics is an emerging field of research downstream from genomics, proteomics and transcriptomics. A metabolome is a quantitative collection of low molecular weight compounds, such as metabolic substrates and products, lipids, small peptides, vitamins, and other protein cofactors, generated by metabolism. A metabolome is downstream from a transcriptome and a proteome and thus any changes from a normal state are amplified and are numerically more tractable. Metabolomics can be a precise, consistent, and quantitative tool to examine and describe cellular growth, maintenance, and function.

Generally, bodily fluid and especially urine metabolomics represents a much less invasive method of testing compared to tissue metabolomics.

The present invention uses bodily fluid metabolomics to identify subjects having or at risk of developing CRC and/or colorectal polyps. This is beneficial in the management of the risk of CRC and/or colorectal polyps, both in prevention and treatment. The use of bodily fluid metabolomics in the present invention has a number of potential benefits. Obtaining a bodily fluid (e.g., urine) sample and its analysis are relatively simple, non-invasive for many of the bodily fluids, and cost efficient compared to the existing methods for assessing presence or absence of CRC and/or colorectal polyps. The invention also permits monitoring of individual susceptibility to CRC prior to resorting to, or in combination with, conventional screening methods, and provides for population-based monitoring of CRC and/or colorectal polyps.

A wide range of analytical techniques to assay and quantitate components of a metabolome and to extract useful metabolite profiles from the data are available, including e.g. liquid and gas chromatography coupled with mass spectrometry (LC-MS or GC-MS), nuclear magnetic resonance (NMR) spectroscopy, high performance liquid chromatography (HPLC), thin layer chromatography (TLC), electrochemical analysis, refractive index spectroscopy, ultra-violet spectroscopy, fluorescent analysis, radiochemical analysis, near-infrared spectroscopy and light scattering analysis. The outputs from such analytical techniques can be further analyzed using multivariate analysis such as, e.g., principal component analysis (PCA), partial least squares discriminant analysis (PLS-DA), sparse PLS-DA (sPLS-DA), and orthogonal partial least squares (OPLS).

Statistically validated metabolite profiles obtained from a reference population of known CRC and/or colorectal polyp status can be used as a reference to assess the presence or absence of CRC and/or colorectal polyps in a subject. For example, a reference population may be composed of healthy subjects (i.e., subjects known or assessed by other means [e.g., colonoscopy] to be free of CRC and/or colorectal polyps), or alternatively may be composed of subjects already identified to have or to be predisposed to developing CRC or colorectal polyps. In some embodiments, the reference profile is composed of subjects matched to the subject being tested by one or more parameters selected from age, gender, ethnicity, smoking status, family history, Body Mass Index (BMI), etc. This assessment can be performed by: (a) providing a bodily fluid (e.g., urine) sample from a subject that is suspected to have or be predisposed to developing CRC and/or colorectal polyps; (b) obtaining a metabolite profile from said bodily fluid sample; (c) comparing said metabolite profile with a reference metabolite profile; and (d) assessing, based on said comparison in step (c), whether said subject has or is predisposed to developing CRC and/or colorectal polyps.

Providing and Processing Urine Samples

Bodily fluid samples can be collected from subjects that are known or suspected to have CRC or colorectal polyps, and from subjects without CRC or colorectal polyps, by known protocols. The subjects of this invention include both sexes of animal species that are susceptible to CRC and/or colorectal polyps, including humans.

In addition to providing a bodily fluid sample, subjects can take a fecal occult blood test (FOBT), fecal DNA tests, blood septin 9 tests, flexible sigmoidoscopy, air-contrast barium enema, computed tomography colonography (CTC), fecal immune testing (FIT), and/or colonoscopy, the results of which can be used to determine classification of subjects into one of the groups of: subjects without CRC and/or colorectal polyps (normal group); subjects having colorectal polyps in general (polyp group); or subjects having adenomatous polyps specifically (adenomatous group). Pathology of resected surgical specimens can be used as the standard to classify subjects into a group where subjects have CRC (CRC group). Relevant clinical information such as age, gender, family history, comorbidities, medications etc. can be obtained from study questionnaires and subjects' medical charts, which could also be used to determine classification of subjects. Such testing can be used in the development of reference metabolite profiles and can also be used as an adjunct to screening test subjects by the methods of the invention to confirm or further refine a diagnosis of CRC and/or colorectal polyps.

Bodily fluid samples can be collected from subjects any time, e.g., during routine screening or in connection with a regular check-up or visit to a physician, or prior to or together with administration of treatment, such as the administration of a medicine or performance of surgery. For example, urine samples can be collected one or more times for a separate or combined analysis, e.g., 15-700 ml each time. Urine sample collection containers can vary in size and shape, but ideally can accommodate e.g. 20-1,000 ml of urine sample. Typically, bodily fluid sample containers used in the methods of the present invention are sterile. If desired, sample containers can be pre-filled or treated with agents for preventing contamination of the samples by microorganisms such as bacteria and fungi while the samples are waiting to be stored, or such agents can be added after sample collection. Metabolomic analysis of the collected samples may occur immediately or the samples may be processed for storage and later analysis. For example, the whole or part of the sample could be stored in a freezer at −5° C. to 10° C. within 0-48 hours of collection, or could be frozen at −120° C. to −10° C. within 0-48 hours of collection, or could be processed with chemicals (e.g., in the case or urine samples, processed with an extraction solvent [such as, e.g., water with 10 mM ammonium formate, pH3]) for future analysis or use before being stored. If samples have been stored frozen, they may be thawed (e.g., at room temperature for 12-48 hours), prior to analysis.

For example, over 1000 urine samples were acquired previously as part of a regional colon cancer screening program in Edmonton, Canada (SCOPE®, Stop Colorectal Cancer through Prevention and Education). Urine was aliquoted and frozen at −80° C. within 1 hour of collection.

In some embodiments, bodily fluid (e.g., urine) samples may be processed prior to analysis. For example, for LC-MS acquisition, a simple approach of dilution and filtration can be used for sample preparation. Bodily fluid (e.g., urine) samples can be centrifuged at 10,000 g for 3 mins. 10 µL of each urine supernatant can then be added to proper container. 10 µL internal standards (ISTD) can be added to each sample to account for matrix effect and facilitate the absolute quantification. The mixture can then be extracted with 200 µL of extraction solvent (water with 10 mM Ammonium formate, pH3) and filtered through 0.45 m member filter before LCMS injection. Other useful bodily fluid sample processing methods include, without limitation, centrifugation, liquid-liquid extraction, solid phase extraction, derivatization, and any combinations thereof. See, e.g., Bouatra et al., (2013) The Human Urine Metabolome, PLoS ONE, 8(9):e73076 (https://doi.org/10.1371/journal.pone.0073076).

Obtaining a Metabolite Profile from a Bodily Fluid Sample

The analytical techniques that make it possible to obtain metabolite profiles from the bodily fluid samples can include one or a combination of, but not limited to, mass spectrometry (MS) coupled with gas chromatography (GC-MS) or liquid chromatography (LC-MS), HPLC, NMR spectroscopy, TLC, electrochemical analysis, refractive index spectroscopy, ultra-violet spectroscopy, fluorescent analysis, radiochemical analysis, near-infrared spectroscopy and light scattering analysis. The outputs obtained from such analyses can be further analyzed using analytical tools to aid in the characterization of differences of metabolite profile between samples related to CRC or colorectal polyps. Such analytical tools include, but are not limited to, multivariate statistical analysis, logistic regression, principal component analysis (PCA), partial least squares discriminant analysis (PLS-DA), sparse PLS-DA (sPLS-DA) and orthogonal partial least squares discriminant analysis (oPLS-DA), support vector machines (SVM), discriminant analysis, kernel methods, nonparametric methods, tree-based methods, generalized linear models, generalized additive modes, fuzzy logic based methods, neural networks, and genetic algorithm-based methods. Though HPLC or technologies involving MS can be used for measuring metabolite levels in the sub-molar range, they are often laborious and time consuming as they require that chromatography (liquid or gas) to separate the metabolites be done first, and also require multiple internal standards.

In some embodiments, targeted Liquid chromatography-mass spectrometry (LCMS/MS) methods can be developed to quantify key metabolites (for example, diacetylspermine, kynurenine) in bodily fluid samples using multiple reaction monitoring (MRM). For example, a combination of direct injection mass spectrometry with a reverse-phase LC-MS/MS Kit such as TMIC00UJ can be used. The TMIC00UJ kit is a combination of three assays to identify 140 unique urinary metabolites (see Table 2) indexed by the Human Metabolome Database (www.hmdb.ca). This kit, in combination with an ABI 4000 Q-Trap (Applied Biosystems/MDS Sciex) mass spectrometer, can be used for the targeted identification and quantification of up to 143 different endogenous metabolites including amino acids, acylcarnitines, biogenic amines & derivatives, glycerophospholipids, sphingolipids and sugars, as well as 17 organic acids and ascorbic acid.

As a non-limiting example, the TMIC00UJ kit components can be run on an API4000 Qtrap® tandem mass spectrometry instrument (AB Sciex, Framingham, MA) coupled with a Waters UPLC system (Waters Limited, Mississauga, ON). Urine samples can be thawed on ice, vortexed, then centrifuged at 13,000×g. Each plate can contain, for example, 82 unique urine samples as well as 1 solvent blank solution, 3 matrix solutions, 7 calibration solutions (Cal 1-Cal 7), and 3 quality control (QC) samples. Phosphate-buffered saline (PBS 1×, pH 7.4) is used as the matrix solution. Metabolite quantification can be achieved using the AB Sciex Analyst® software, version 1.6.2. During quantification, each metabolite can be identified using the internal standard and compared against the established calibration curve. The lower limits of detection (LLOD) and upper limit of detection can be calculated as three times the value of the matrix solutions.

NMR spectroscopy is another tool for metabolonomics study. It can quantify a large number of metabolites simultaneously, requires only one standard, and is generally faster to yield statistical analysis results such as PCA and/or OPLS plots.

In some embodiments, urine samples may be processed prior to NMR analysis. For example, for non-automated (manual) NMR acquisition, about 100-1,000 µL urine sample can be taken from the collected and/or stored sample, then diluted with an internal standard at a ratio of e.g. 1:1-1:20 (v/v). The internal standard can include e.g. 1-20 mM of sodium 2,2-dimethyl-2-silapentane-5-sulfonate (DSS) or its salt form, 4,4-Dimethyl-4-silapentane-1-ammonium trifluoroacetate (DSA), or Trimethylsilyl propionate (TSP). Agents for preventing microbial contamination can also be added. Such additions can include e.g. 10-200 mM imidazole, or 0.1-0.5% or 0.5-5 µM of sodium azide. The total volume can be e.g. 100-1,300 µL. The sample for NMR analysis can be stored in a freezer at e.g. 1-6° C. The same process applies to the automated (robotic) NMR acquisition. On the day of NMR acquisition, the pH of each sample is measured. Various concentrations of acids and bases, for example, but not limited to, HCl and NaOH, can be added to the samples to achieve a pH between e.g. 6.7 and 6.8 to minimize chemical exchange as the chemical shift can change with pH. An aliquot of e.g. 100-1,000 µL of the samples can be placed in NMR tubes and capped for the samples for both non-automated and the automated NMR.

One-dimensional NMR spectra can be acquired. After the spectra are obtained, the pH of each sample can be rechecked to ensure that the pH has not shifted a significant amount. This data can be recorded to be referenced if a particular sample would produce an unexpected spectrum. Samples can be frozen and stored again at a sub-zero temperature.

In some embodiments, the metabolite profile includes measurements of levels in a bodily fluid sample of at least any 1, 2, 3, 4, 5, 6, 7, 8, 9, 10, 11, 12, 13, 14, 15, 16, or 17 metabolites selected from diacetylspermine, proline, C14:1, kynurenine, glucose, 3-(3-Hydroxyphenyl)-3-hydroxypropanoic acid (HPHPA), aspartic acid, beta-hydroxybutyric acid, 3,4-dihydroxyl phenylalanine (DOPA), 4-hydroxyproline, aminoadipic acid, putrescine, indole acetic acid, hippuric acid, citric acid, sarcosine, and butyric acid.

In some embodiments, the metabolite profile includes measurements of levels in a bodily fluid sample of at least any 1, 2, 3, or 4 metabolites selected from the group consisting of: diacetylspermine, proline, kynurenine, and glucose.

In some embodiments, the metabolite profile includes measurements of levels in a bodily fluid sample of diacetylspermine and/or kynurenine. In some embodiments, the metabolite profile includes measurements of levels in a bodily fluid sample of diacetylspermine. In some embodiments, the metabolite profile includes measurements of levels in a bodily fluid sample of kynurenine. In some embodiments, the metabolite profile includes measurements of levels in a bodily fluid sample of diacetylspermine and kynurenine.

In some embodiments, the metabolite profile includes measurements of levels in a bodily fluid sample of any metabolites disclosed in U.S. Pat. No. 10,267,800 and WIPO Publication No. WO/2018/184112, the contents of each of which are hereby incorporated by reference in their entirety for all purposes.

Identification of Metabolites for a Reference Metabolite Profile

The present invention involves the discovery that metabolite profiles in bodily fluid (e.g., urine) samples of subjects having or predisposed to developing CRC and/or colorectal polyps can be reliably distinguished from metabolite profiles in the bodily fluid (e.g., urine) samples of healthy subjects (i.e. those without CRC and/or colorectal polyps) such that this distinction can be used to assess whether a particular subject has or is predisposed to developing CRC and/or colorectal polyps. One or more reference profiles concerning metabolites present in the bodily fluid of a reference population known either to be free of CRC and/or colorectal polyps or to have or be predisposed to developing CRC or colorectal polyps is developed, which can then be used for comparison against a corresponding metabolite profile generated from the bodily fluid of a test subject. By analyzing the metabolite content of the bodily fluid of subjects of known CRC or colorectal polyp status, it is then possible to compare this to the content of the same metabolites in subjects of a different CRC or colorectal polyp status, thus identifying metabolites which correlate significantly with the CRC or colorectal polyp status of an individual. In the illustrative examples herein, 240 metabolites were considered and 69 found to be of particular significance. However, bodily fluids such as urine contain thousands of metabolites, and the techniques described can be employed to assess whether other metabolites are similarly diagnostic of CRC and/or colorectal polyps.

Thus, in one aspect, the invention provides a method for identifying bodily fluid (e.g., urine) metabolites indicative of the presence or absence of CRC and/or colorectal polyps, the method comprising: (a) providing a bodily fluid sample from a subject; (b) obtaining a metabolite profile from the bodily fluid sample; (c) comparing the metabolite profile with a reference metabolite profile; and (d) identifying, based on the comparison in step (c), one or more metabolites in the metabolite profile that are indicative of the presence of or predisposition to in said subject of colorectal cancer and/or colorectal polyps.

Quantification of metabolite levels, e.g. by concentration or in absolute amount, can be done once the analysis data is available from, for example, but not limited to, GC-MS, LC-MS, HPLC, NMR spectroscopy, TLC, electrochemical analysis, refractive index spectroscopy, ultra-violet spectroscopy, fluorescent analysis, radiochemical analysis, near-infrared spectroscopy and light scattering analysis. The quantification data can be used to identify and to set a standard to determine a reference metabolite profile based on bodily fluid samples obtained from subjects known to be free of CRC and/or colorectal polyps.

For example, once the spectra are acquired from NMR spectroscopy, quantification of metabolites can be done using tools that compare the integral of a known reference signal, such as DSS, DSA or TSP, with signals derived from a library of compounds to determine level relative to the reference signal. The tools can include software such as Chenomx NMRSuite v4.6 software. The quantification process can be done by more than one individual for reading and verification to optimize accuracy.

Levels of the specific metabolites over or below a determined critical value, either in concentration or in amount, can indicate the presence of CRC or colorectal polyps in general or adenomatous polyps in particular. The concentrations or the amount of the metabolites can be interpreted independently using an individual cut-off for each metabolite or they can be interpreted collectively. Metabolite concentrations or amounts obtained can be used as they are (i.e., as the raw data) or be normalized. For example, the concentration or amount of a metabolite can be log-transformed to normalize the concentrations or amounts to the concentration or the amount of other metabolites. The metabolites can also be normalized to the concentration of all metabolites minus the concentration of selected compounds such as e.g. urea to obtain similar results.

Multivariate statistical analysis can be applied to the collected data or complex spectral data to identify differences arising between the groups of data sets obtained from the bodily fluid sample. The metabolite measurements in samples from subject having CRC or colorectal polyps in general or adenomatous polyps specifically can be compared to metabolite measurements in samples from subjects without CRC or colorectal polyps to identify metabolites that significantly contribute to the separation of different groups. Data comparison can be performed using any appropriate tools that fulfill the purpose. Non-limiting examples of such tools include, e.g., multivariate statistical analysis, logistic regression, principal component analysis (PCA), partial least squares discriminant analysis (PLS-DA), sparse PLS-DA (sPLS-DA) and orthogonal partial least squares discriminant analysis (oPLS-DA), support vector machines (SVM), discriminant analysis, kernel methods, nonparametric methods, tree-based methods, generalized linear models, generalized additive modes, fuzzy logic based methods, neural networks, and genetic algorithm-based methods. Software that can perform one or more of such analyses, e.g., Simca-P+, can be used.

An optimized multivariate cut-off for the underlying combination of metabolites can be used to discriminate a cancerous or pre-cancerous state from a healthy state. Upon determination of which specific metabolites are the significant contributors to the data separation between the CRC group and the normal group samples or the polyp group and the normal group samples or the adenoma group and the normal group samples, one or more profiles of these specific metabolites can be established. One or more metabolite profiles or its combination can be used as a reference metabolite profile to assess CRC or colorectal polyps in general or adenomatous polyps in particular in a subject.

In some embodiments, metabolites that can be used in separating normal group from CRC group include, but are not limited to, diacetylspermine, proline, C14:1, kynurenine, glucose, 3-(3-Hydroxyphenyl)-3-hydroxypropanoic acid (HPHPA), aspartic acid, beta-hydroxybutyric acid, 3,4-dihydroxyl phenylalanine (DOPA), 4-hydroxyproline, aminoadipic acid, putrescine, indole acetic acid, hippuric acid, citric acid, sarcosine, and butyric acid.

However, not all features of the metabolite analysis results are always required for a proper diagnosis of CRC or colorectal polyps in general or adenomatous polyps specifically. Since there would be an incremental cost to obtaining more information about a subject's bodily fluid metabolite profile, it may be beneficial to use the minimal number of metabolites possible. In order to determine which specific metabolites are the strongest contributors to the data separation between the CRC group and the normal group samples or the polyp group and the normal group samples or the adenoma group and the normal group samples, further data analysis can be performed. This further data analysis could be made by an appropriate analytical method such as, but not limited to, a volcano plot (i.e., a combination of the fold changes (FC) analysis and t-test, which provides a preliminary overview about features that are potentially significant in discriminating two groups).

There are many ways to evaluate a selected metabolite profile to assess whether a subject has or is predisposed to developing CRC and/or colorectal polyps. The values measured for metabolites can be mathematically combined and the combined value can be correlated to the underlying diagnostic question. Metabolite values may be combined by any appropriate mathematical method. Mathematical methods for correlating a metabolite combination to a disease can employ methods such as, but not limited to, discriminant analysis (DA) (i.e. linear-, quadratic-, regularized-DA), Kernel Methods (i.e., SVM), Nonparametric Methods (i.e. k-Nearest-Neighbor Classifiers), PLS (Partial Least Squares), Tree-Based Methods (i.e. Logic Regression, CART, Random Forest Methods, Boosting/Bagging Methods), Generalized Linear Models (i.e. Logistic Regression), Principal Components based Methods (i.e. SIMCA), Generalized Additive Models, Fuzzy Logic based Methods, Neural Networks and Genetic Algorithms based Methods. For the SVM model, the linear coefficients of each feature in an SVM classifier can be used to select the most important features. Those features that had the largest absolute value can be selected, and the SVM model can be re-calculated using only the selected features and the training set if necessary.

When comparing test results from two different populations, for example, one with a disease and the other without the disease, a perfect separation between the two groups is rarely observed. Indeed, the distribution of the test results will overlap. Therefore, when a cut-off point or criterion value to discriminate between the two populations is selected and applied, there will be some cases with the disease correctly classified as positive (True Positive fraction), but some cases with the disease will be classified negative (False Negative fraction). On the other hand, some cases without the disease will be correctly classified as negative (True Negative fraction), but some cases without the disease will be classified as positive (False Positive fraction).

The diagnostic performance of such a test, or the accuracy of a test to discriminate diseased groups from healthy groups, can be evaluated using tools such as ROC curve analysis. The ROC curve is a graphical representation of the spectrum of sensitivities and specificities generated using the various cut-offs, using the sensitivity as the y-axis and 1-specificity as the x-axis. In an ROC curve the true positive rate (Sensitivity) is plotted in function of the FP rate (100-Specificity) for different cut-off points. Each point on the ROC curve represents a sensitivity/specificity pair corresponding to a particular decision threshold. A test with perfect discrimination (no overlap in the two distributions) has a ROC curve that passes through the upper left corner (100% sensitivity, 100% specificity). Therefore, qualitatively, the closer the plot is to the upper left corner, the higher the overall accuracy of the test. Area under the ROC curve (AUC) reflects the accuracy of the test and is displayed on the left lower corner of the plot. An AUC of 0.9 to 1 represents an excellent diagnostic test whereas an AUC of 0.8-0.9 represents a good test and an AUC of 0.7 to 0.8 represents a fair test.

Standard machine learning methodology of using an external data set can be used to evaluate how well the predictor could predict labels for new unlabeled instances. A dataset can be divided into two thirds training data and one third testing data. These two data sets can be balanced for age, sex, and class distribution.

Further, using MS can allow for development and validation of a clinically scalable test for the detection of CRC and/or colorectal polyps (e.g., adenomatous polyps), which would be suitable for population-based colorectal cancer screening. Compared to other methods, MS is sensitive, high throughput, and cost-effective. In addition, the ability to develop multianalyte panels using a single MS method offers additional time, labor, and expense savings, for which immunosuppressant assays are a great example.

The prediction threshold for the developed algorithm can be adjustable, to vary the tradeoff between sensitivity and specificity. As sensitivity increases, more samples are being predicted as positive (i.e. requiring colonoscopy). Meanwhile the specificity drops. To optimize the predictor to a specific market, requirements for the test's sensitivity, specificity, or Predictive Rate must be met. For example, predictive performance of a PolypDx™ test was compared against the given requirements. A prediction threshold on the training data results (along the ROC curve) was chosen, and then evaluated on the testing data set. The results are summarized in Table 6. The thresholds tested were sensitivity at 70, 80, and 90%, and specificity at 70, 80 and 90%. The results show that this protocol for picking a threshold generalizes well to the testing set. This is likely due to the nature of the LASSO linear predictor. For more complex predictors, such as Random Forests, this threshold picking may not generalize well.

Development of Reference Metabolite Profiles

In some embodiments, a reference metabolite profile is directed to assessing whether a subject has or is predisposed to developing CRC and/or colorectal polyps.

In some embodiments, the reference metabolite profile includes measurements of levels in a bodily fluid (e.g., urine) sample of at least any 1, 2, 3, 4, 5, 6, 7, 8, 9, 10, 11, 12, 13, 14, 15, 16, or 17 metabolites selected from diacetylspermine, proline, C14:1, kynurenine, glucose, 3-(3-Hydroxyphenyl)-3-hydroxypropanoic acid (HPHPA), aspartic acid, beta-hydroxybutyric acid, 3,4-dihydroxyl phenylalanine (DOPA), 4-hydroxyproline, aminoadipic acid, putrescine, indole acetic acid, hippuric acid, citric acid, sarcosine, and butyric acid.

In some embodiments, the reference metabolite profile includes measurements of levels in a bodily fluid (e.g., urine) sample of at least any 1, 2, 3, or 4 metabolites selected from the group consisting of: diacetylspermine, proline, kynurenine, and glucose.

In some embodiments, the reference metabolite profile includes measurements of levels in a bodily fluid (e.g., urine) sample of diacetylspermine and/or kynurenine. In some embodiments, the reference metabolite profile includes measurements of levels in a bodily fluid (e.g., urine) sample of diacetylspermine. In some embodiments, the reference metabolite profile includes measurements of levels in a bodily fluid (e.g., urine) sample of kynurenine. In some embodiments, the reference metabolite profile includes measurements of levels in a bodily fluid (e.g., urine) sample of diacetylspermine and kynurenine.

Generally, the more metabolites that are assessed, the more accurate will be the assessment of CRC and/or colorectal polyps. In exemplary embodiments, more than 140 metabolites were considered, and 17 metabolites were used to assess whether a subject has or is predisposed to developing CRC or colorectal polyps. Indeed, other, or additional metabolites beyond these metabolites identified can be included in the metabolite profile. However, as noted above, this involves greater effort and cost. In many instances, a less accurate, specific, or detailed assessment may be sufficient, particularly if the assessment is only preliminary in nature, or is to be conducted together with or followed by another diagnostic test, such as colonoscopy. Further, a test involving the assessment of fewer metabolites may be more readily reduced to a simplified kit or test that can be used by a subject at home, or by a medical practitioner at the point of care, without need for sending a bodily fluid sample to a laboratory for analysis.

In some embodiments of the invention, it is the concentration (e.g., measured in $\mu M$) of the bodily fluid (e.g., urine) metabolites that is measured, and a higher or lower concentration of the metabolite in the bodily fluid of a test subject relative to that in reference metabolite profile (based either on raw or normalized concentrations) is indicative of CRC or even indicative of a specific stage of CRC (e.g., an early stage or a late stage).

In some embodiments, a 2-fold or more elevated level of any one or more metabolites selected from the group consisting of diacetylspermine, proline, C14:1, kynurenine, glucose, beta-hydroxybutyric acid, 3,4-dihydroxyl phenylalanine (DOPA), 4-hydroxyproline, putrescine, citric acid and sarcosine is indicative that the subject has or is predisposed to developing CRC and/or colorectal polyps. For instance, referring to Table 3, it will be seen that the level of diacetylspermine in the urine of individuals with CRC was 10.75-fold higher than the level of diacetylspermine in the urine of "normal" subjects without CRC.

In some embodiments, a 2-fold or more reduced level of any one or more metabolites selected from the group consisting of 3-(3-Hydroxyphenyl)-3-hydroxypropanoic acid (HPHPA), aspartic acid, aminoadipic acid, indole acetic acid, hippuric acid, and butyric acid is indicative that the subject has or is predisposed to developing CRC and/or colorectal polyps. For instance, referring to Table 3, it will be seen that the level of HPHPA in the urine of individuals with CRC was 0.33 of the level of HPHPA in the urine of "normal" subjects without CRC.

In some embodiments, the reference metabolite profile is designed to identify subjects having or predisposed to colorectal polyps (e.g., adenomatous or hyperplastic).

Assessing Whether a Subject has or is Predisposed to Developing CRC and/or Colorectal Polyps The invention provides methods for assessing whether a subject has or is predisposed to developing CRC and/or colorectal polyps, the method comprising: (a) providing a bodily fluid (e.g., urine) sample from said subject; (b) obtaining a metabolite profile from said bodily fluid (e.g., urine) sample; (c) comparing said metabolite profile with a reference metabolite profile; and (d) assessing, based on said comparison in step (c), whether said subject has or is predisposed to developing CRC and/or colorectal polyps.

Bodily fluid samples can be obtained as described above. Comparison of the metabolite profile from the subject to the reference metabolite profile allows for assessment of whether the subject has or is predisposed to developing CRC and/or colorectal polyps.

Merely by way of an illustrative example, the method might be a method for assessing whether a subject has or is predisposed to developing CRC and/or colorectal polyps. A bodily fluid (e.g., urine) sample could be taken and levels of the following metabolites measured: diacetylspermine, proline, C14:1, kynurenine, glucose, 3-(3-Hydroxyphenyl)-3-hydroxypropanoic acid (HPHPA), aspartic acid, beta-hydroxybutyric acid, 3,4-dihydroxyl phenylalanine (DOPA), 4-hydroxyproline, aminoadipic acid, putrescine, indole acetic acid, hippuric acid, citric acid, sarcosine, and butyric acid. The level of each of these metabolites in the subject's sample(s) is then compared to the levels of the corresponding metabolites in the reference metabolite profile. Detection of a higher level of any one or more of diacetylspermine, proline, C14:1, kynurenine, glucose, beta-hydroxybutyric acid, 3,4-dihydroxyl phenylalanine (DOPA), 4-hydroxyproline, putrescine, citric acid and sarcosine in the subject's metabolite profile than in the reference metabolite profile may indicate that the subject has or is predisposed to developing CRC and/or colorectal polyps. Similarly, a lower level of any one or more of 3-(3-Hydroxyphenyl)-3-hydroxypropanoic acid (HPHPA), aspartic acid, aminoadipic acid, indole acetic acid, hippuric acid, and butyric acid in the subject's metabolite profile than in the reference metabolite profile may indicate that the subject has or is predisposed to developing CRC and/or colorectal polyps.

Metabolomic-based determination using the methods of the present invention that the subject has or is predisposed to developing CRC and/or colorectal polyps can be further verified using one or more additional diagnostic methods. Non-limiting examples of such additional diagnostic methods include, e.g., fecal occult blood test (FOBT), fecal immunochemical test (FIT), fecal DNA tests, flexible sigmoidoscopy, blood septin 9 test, air-contrast barium enema, computed tomography colonography (CTC), and colonoscopy. In one specific embodiment, the additional diagnostic method is a colonoscopy.

In some embodiments, metabolomic-based determination using the methods of the present invention is followed by administering a specific treatment to the subject and/or by inclusion of the subject in a clinical trial.

Diagnostic Kits

The invention also provides kits for assessing whether a subject has or is predisposed to developing CRC and/or colorectal polyps. Such kits may comprise one or more reagents for detecting the presence and/or level of one or more metabolites in a bodily fluid sample of a subject (e.g., a set of calibrant solutions with known level of metabolites and/or a set of quality controls samples and/or a mixture of internal standards), and may include instructions for use of the kit for assessing whether a subject has or is predisposed to developing CRC and/or colorectal polyps.

The most reliable results are likely obtained when bodily fluid (e.g., urine) samples are processed, e.g. by NMR spectroscopy, mass spectrometer, in a laboratory setting. For instance, a bodily fluid sample might be obtained from a subject in the office of a medical practitioner and then sent to a hospital or commercial medical laboratory for further testing. However, in many instances, it may be desirable to provide immediate results in a clinician's office or to permit a subject to conduct testing at home. The need for a test that is portable, pre-packaged, disposable, usable by a subject without assistance or direction, etc. may in some instances be of more importance than a high degree of accuracy. In many instances, particularly where there will be follow-up with a medical practitioner, a preliminary test, even one with reduced sensitivity and/or specificity may be sufficient. Thus, an assay presented in kit form may involve detection and measurement of a relatively small number of metabolites, to reduce the complexity and cost of the assay.

Any form of a kit capable of detecting metabolites as described herein may be used. Typically, the kit will quantitate the bodily fluid (e.g., urine) metabolites to determine whether they are higher or lower in concentration or in amount than a predetermined threshold value. Such kits may take the form of a test strip, dip stick, cassette, cartridge, chip-based or bead-based array, multi-well plate, or series of containers, or the like. One or more reagents can be provided to detect the presence and/or concentration and/or amount of selected metabolites. The subject's bodily fluid (e.g., urine) may be dispensed directly onto the assay or indirectly from a stored sample. The presence or absence of a metabolite above or below a pre-determined threshold may be displayed e.g. by a chromogenic, fluorogenic, electrochemiluminescent or other output, e.g. as in an enzyme immunoassay (EIA) such as an enzyme-linked immunoassay (ELISA).

In an embodiment, a kit may comprise a solid substrate, such as e.g. a chip, slide, array, etc., with reagents capable of detecting and/or quantitating one or more bodily fluid (e.g., urine) metabolites immobilized at predetermined locations on the substrate. By way of an illustrative example, a chip can be provided with reagents immobilized at discrete, predetermined locations for detecting and quantitating in a bodily fluid (e.g., urine) sample the level of diacetylspermine and kynurenine. As discussed above, elevated levels of these metabolites were found in bodily fluid (e.g., urine) samples of subjects with CRC. The chip may be configured such that a detectable output (e.g. color change) is provided only if the level of one or more of these metabolites is over a threshold value, the threshold value being selected to distinguish between a metabolite level indicative of healthy subjects and those having or predisposed to developing CRC and/or colorectal polyps. Thus, the presence of a detectable output such as a color change provides an immediate indication that the sample contains significantly elevated levels of one or more relevant metabolites, indicating that the subject has or is predisposed to developing CRC and/or colorectal polyps.

Systems for Performing the Assessment of CRC or Colorectal Polyps

In an embodiment, the invention provides a system for assessing whether a subject has or is predisposed to developing CRC and/or colorectal polyps. Such a system may comprise:
  (a) a CRC- and/or colorectal polyps-assessing apparatus including a control unit and a memory unit to assess a CRC or colorectal polyps state in a subject; and
  (b) an information communication terminal apparatus that provides data on the presence and/or concentration and/or amount of metabolites in a bodily fluid (e.g., urine) sample from the subject connected to each other communicatively, wherein the information communication terminal apparatus includes:
  (a) a data sending unit that transmits the data on the presence and/or concentration and/or amount of metabolites in the sample to the CRC- and/or colorectal polyps-assessing apparatus; and
  (b) an assessment result-receiving unit that receives the assessment result of the CRC and/or colorectal polyps state of the subject transmitted from the CRC- and/or colorectal polyps-assessing apparatus,
  wherein the control unit of the CRC- and/or colorectal polyps-assessing apparatus includes:
  (a) a data-receiving unit that receives the data on the metabolite concentration and/or amount of the sample transmitted from the information communication terminal apparatus;
  (b) a discriminant value-calculating unit that calculates a discriminant value that is a value of multivariate discriminant, based on both the concentration and/or amount value of the metabolite in the sample received by the data-receiving unit and a multivariate discriminant with the concentration and/or amount of the metabolite as explanatory variable stored in the memory unit;
  (c) a discriminant value criterion-assessing unit that assesses the CRC or colorectal polyps state in the subject, based on the discriminant value calculated by the discriminant value-calculating unit; and
  (d) an assessment result-sending unit that transmits the assessment result of the subject obtained by the discriminant value criterion-assessing unit to the information communication terminal apparatus.

Evaluation of Efficacy of Pharmaceutical Agents and/or Physical Treatments and/or Surgical Treatment Metabolomic analysis is ideal for identification of and evaluation of the effects of potential pharmaceutical agents and/or new physical (e.g., radiation) and/or surgical treatments against CRC and/or colorectal polyps (such as e.g., adenomatous polyps). Bodily fluid (e.g., urine) samples can be taken one or more times, by methods described previously herein, from a subject before and after treatment. The treatment can include administration of one or more pharmaceutical agents at one or more doses, and/or carrying out one or more physical and/or surgical treatments, to or on a subject. The administration of pharmaceutical agents can be made in many different ways including, but not limited to, injection, oral administration, patch or ointment application.

The metabolite profiles obtained from the samples can be compared with each other and/or with the metabolite profile from subjects without CRC and/or colorectal polyps. The comparison can indicate the efficacy of the pharmaceutical agents and/or the physical treatment and/or surgical treatment through changes of the metabolite profile in bodily fluid (e.g., urine) samples of the subject. Also, comorbidities and medications of a subject can be studied in subsequent analyses to determine their effects on the metabolomic test results and specifically whether they contribute to discordant results. In addition, the metabolite profiles of the CRC and/or colorectal polyp samples can be correlated with operative and histological findings to determine whether CRC and/or colorectal polyp location or stage can change a metabolite profile.

Treatment Methods of the Invention

In conjunction with the diagnostic methods disclosed herein, the invention also provides methods for treating CRC and/or colorectal polyps in the subject. In some embodiments of the invention, metabolomic-based determination of CRC and/or colorectal polyps using the methods of the present invention is followed by administering a specific treatment to the subject and/or by inclusion of the subject in a clinical trial.

In the context of the present invention insofar as it relates to any of the disease conditions recited herein, the terms "treat", "treatment", and the like mean to relieve or alleviate at least one symptom associated with such condition, or to slow or reverse the progression of such condition, or to arrest, delay the onset (i.e., the period prior to clinical manifestation of a disease) and/or reduce the risk of developing or worsening a disease.

The treatment administered can be any treatment for CRC and/or colorectal polyps and any combination of various treatments.

In some embodiments, the treatment is a surgical removal of CRC tumor or colorectal polyp. The great majority of benign colon and rectal polyps are small or moderate sized and can be removed through the colonoscope in the outpatient setting. Very small polyps are destroyed with forceps that grasps and removes small pieces of the rectal lining. Larger polyps are removed most often with a metal snare that is passed through a thin insulated hollow plastic tube. The snare and plastic sheath are passed through a channel in the colonoscope to the scopes tip and beyond. The snare is placed around the polyp and tightened while electric current is passed through the wire. This cauterizes the stalk of the polyp while it is being cut. Polyps can also be directly burned or cauterized with heat or electric current.

In some embodiments, the treatment is a radiation therapy.

In some embodiments, treatments include administering at least one pharmacological/chemotherapeutic agent that is directed to the treatment of CRC. One or more different agents may be co-administered (e.g., sequentially or simultaneously). Non-limiting examples of such chemotherapeutic agents include oxaliplatin, irinotecan, capecitabine, tegafur, leucovorin, trifluridine, tipiracil hydrochloride, lanreotide acetate, arfolitixorin, 5-fluorouracil, raltitrexed, antibodies (such as, for example, bevacizumab, cetuximab, ipilimumab, monalizumab, oleclumab, panitumumab, ramacurimab, and biosimilars thereof) or checkpoint inhibitors (such as, for example, avelumab, atezolizumab (MPDL3280A), camrelizumab, durvalumab, nivolumab, pembrolizumab, pidilizumab, and biosimilars), inhibitors with antineoplastic activities (such as, for example, BRAF inhibitors, MEK inhibitors (e.g., binimetinib), TGF beta inhibitors (e.g., LY320082), Akt/ERK inhibitors (e.g., ONC201), tyrosine kinase inhibitors (e.g., aflibercept, apatinib, regorafenib), and pemigatinib), antineoplastic agents with antiretroviral or mmunomodulatory activities (e.g., rintatolimod), and any combinations thereof.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1. Study Participants, Sample Collection, and Patient Characteristics

Adult patients with newly diagnosed CRC (based on preoperative imaging, colonoscopies, and pathology reports of biopsies) were eligible for study inclusion provided they had not received CRC-related treatment. Canadian recruitment was conducted at four tertiary hospitals in the Edmonton region (Grey Nuns Hospital, Misericordia Hospital, University of Alberta Hospital, and the Royal Alexandra Hospital) and included patients from across the prairie provinces (i.e., CRC-CAD cohort). American patients were recruited from the Memorial Sloan Kettering Cancer Center (MSK) in New York City, New York (i.e., CRC-MSK cohort).

Patients diagnosed with CRC provided a urine sample prior to any operation, chemotherapy, radiation, or other cancer-related treatment. Clinical features, such as age, gender, and smoking status, were also collected at this time. Each urine sample was transferred to labelled 1 ml tubes (5×) and frozen at −80° C. within 1 hour of collection. Frozen urine was shipped on dry ice in a standard insulated Styrofoam shipper and immediately transferred to a −80° C. freezer upon arrival at the University of Alberta in Edmonton, Alberta. Pathology reports were reviewed to abstract cancer stage.

Figure 5:
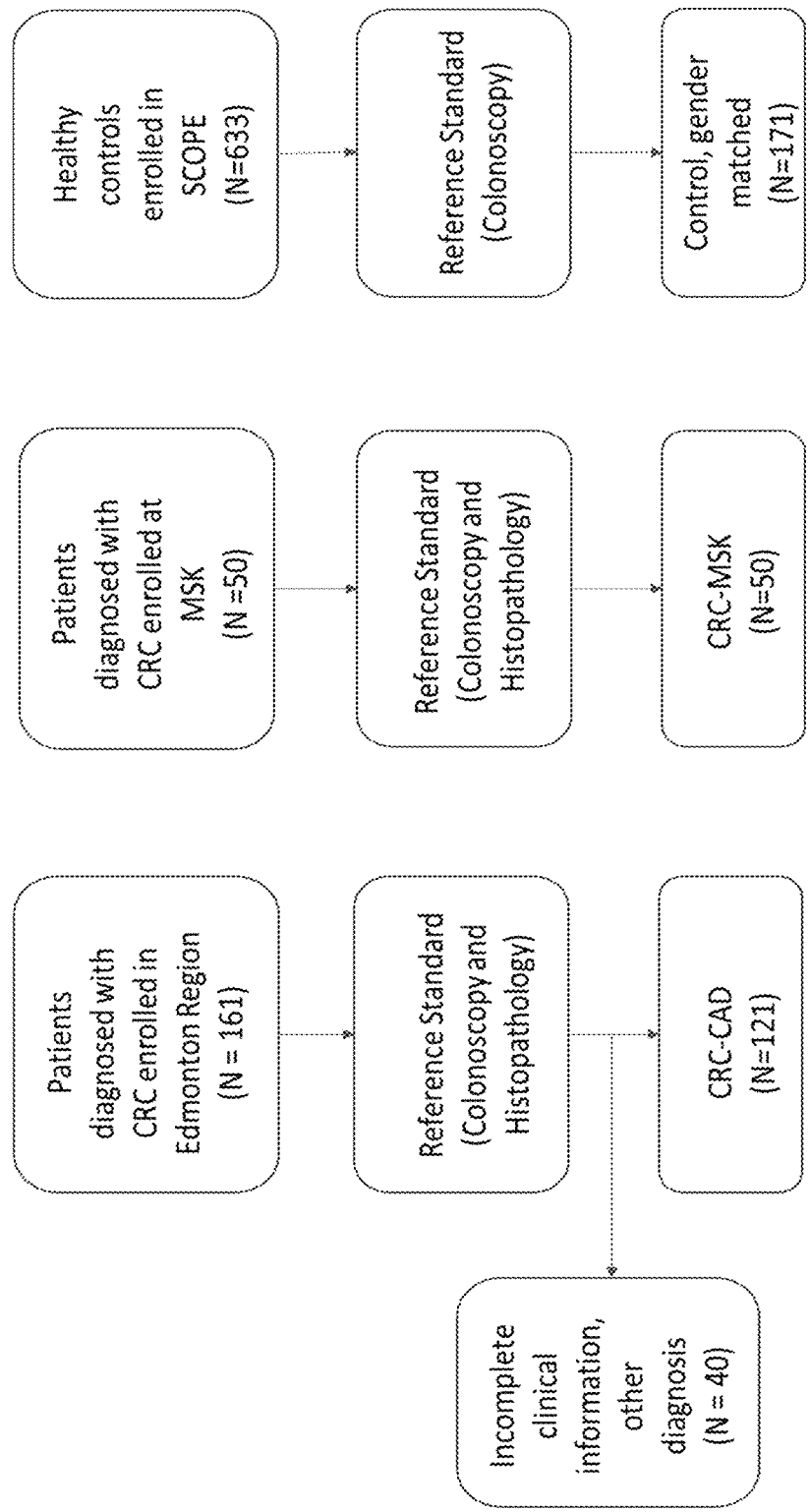
FIG. 5 shows the Case-Control study design.

The healthy controls were selected from a previous population-based study (n=1,000) called Stop COlorectal cancer through Prevention and Education (SCOPE) (24,27-29) The SCOPE program, regional colon cancer screening program (Edmonton, Alberta, Canada) where over 1000 urine samples were collected from April 2008 to October 2009. Study participants (40-74 years of age) of average or increased risk for CRC were recruited. On day of entry, participants provided informed written consent, a midstream urine sample, and completed a demographic survey. Urine was aliquoted and frozen at −80° C. within 1 hour of collection. Colonoscopy was performed 2-6 weeks after the urine collection confirmed that the individuals were classified as normal based upon endoscopy findings and pathology reports. Urine samples from the healthy controls were matched 1:1 to the CRC cases based on gender. A study design chart is shown in FIG. 5.

Ethics approval was obtained from the Health Research Ethics Boards at the University of Alberta (Pro0000514 and Pro00074045) and MSK (IRB #06-107 and #15-209).

In Canada, a total of 161 participants were enrolled of which 40 were excluded due to missing clinical information (i.e., CRC-CAD cohort). A total of 50 samples were collected from patients at Memorial Sloan Kettering (MSK) Cancer Center and used for this study (i.e., CRC-MSK cohort). The 171 CRC samples were matched with 171 urine samples from colonoscopy-confirmed healthy controls. See Table 1 for a summary of clinical characteristics for the participants. Statistical analysis was performed on Control group vs. CRC group. The p-value for gender was 0.63 indicating there was no significant difference in gender between CRC and controls. The p-value for smoking was 0.02 with more current smokers in the CRC group. The p-value for age was $2.83 \times 10^{-13}$ indicating there was a significant difference in age between CRC and controls where the mean age in CRC group was approximately 7 years older than the control group.

TABLE 1

Patient characteristics

|  | Controls | CRC Cases | | |
| --- | --- | --- | --- | --- |
|  |  | CRC-All | CRC-CAD | CRC-MSK |
| Mean Age, yrs (SD) | 58.9 (5.6) | 66.4 (11.5) | 67.4 (10.9) | 63.8 (12.5) |
| Gender, n (%) |  |  |  |  |
| Male | 100 (58.5%) | 89 (52.0%) | 68 (53.7%) | 24 (48.0%) |
| Female | 71 (41.5) | 82 (48.0%) | 59 (46.3%) | 26 (52.0%) |
| Smoking, n (%) |  |  |  |  |
| Current | 12 (7.0%) | 29 (17.0%) | 24 (19.8%) | 5 (10.0%) |
| Prior | 66 (38.6%) | 56 (32.7%) | 38 (31.4%) | 18 (36.0%) |
| Never | 87 (50.9%) | 86 (50.3%) | 59 (48.8%) | 27 (54.0%) |
| By Stage, n (%) |  |  |  |  |
| 0 | — | 3 (1.8%) | 3 (2.5%) | 0 (0.0%) |
| I | — | 30 (17.5%) | 16 (13.2%) | 14 (28.0%) |
| II | — | 50 (29.2%) | 30 (24.8%) | 20 (40.0%) |
| III | — | 57 (33.3%) | 51 (42.1%) | 6 (12.0%) |
| IV | — | 31 (18.1%) | 21 (17.4%) | 10 (20.0%) |
| Total, n | 171 | 171 | 121 | 50 |

Example 2. Metabolite Analysis

Targeted liquid chromatography-mass spectrometry (LC-MS) was performed to quantify urinary metabolites in each sample using the LC-MS kit TMIC00UJ designed and prepared by The Metabolomics Innovation Centre (TMIC) at the University of Alberta in Edmonton, Alberta. Calibration solutions (Cal 1-Cal 7), isotopically labeled standard mix (ISTD), quality control solutions (QC 1-QC 3), LC-MS methods, and standard operating procedures were provided by TMIC. The TMIC00UJ kit was a combination of three assays to identify 140 unique urinary metabolites (see Table 2) indexed by the Human Metabolome Database (www.hmdb.ca). The phenyl isothiocyanate (PITC) assay quantified 47 biologic amines in the LC mode while 75 lipids were semi-quantified in the flow-injection analysis (FIA) mode. The organic acid assay quantified 17 compounds while ascorbic acid was quantified independently.

The TMIC00UJ kit components were run on an API4000 Qtrap® tandem mass spectrometry instrument (AB Sciex, Framingham, MA) coupled with a Waters UPLC system (Waters Limited, Mississauga, ON). Urine samples were thawed on ice, vortexed, then centrifuged at 13,000×g. Each plate contained 82 unique urine samples as well as 1 solvent blank solution, 3 matrix solutions, 7 calibration solutions (Cal 1-Cal 7), and 3 quality control (QC) samples. Phosphate-buffered saline (PBS 1×, pH 7.4) was used as the matrix solution. Metabolite quantification was achieved using the AB Sciex Analyst® software, version 1.6.2. During quantification, each metabolite was identified using the internal standard and compared against the established calibration curve. The lower limits of detection (LLOD) were calculated as three times the value of the matrix solutions. The upper limit of detection was not reached for any metabolite.

For urine amines, lipid and sugar, a targeted quantitative metabolomics approach was applied to analyze the samples using a combination of direct injection mass spectrometry with a reverse-phase LC-MS/MS Kit. This kit, in combination with an ABI 4000 Q-Trap (Applied Biosystems/MDS Sciex) mass spectrometer, can be used for the targeted identification and quantification of up to 143 different endogenous metabolites including amino acids, acylcarnitines, biogenic amines & derivatives, glycerophospholipids, sphingolipids and sugars. A total of 47 biologic amines were quantified in LC mode and a total of 75 lipids were semi-quantified in the FIA mode. The method used combines the derivatization and extraction of analytes, and the selective mass-spectrometric detection using multiple reaction monitoring (MRM) pairs. Isotope-labeled internal standards and other internal standards are used for metabolite quantification. The kit contains a 96 deep-well plate with a filter plate attached with sealing tape, and reagents and solvents used to prepare the plate assay. First 14 wells in the Kit were used for one blank, three zero samples, seven standards and three quality control samples provided with each Kit. Briefly, samples were thawed on ice and were vortexed and centrifuged at 13,000×g. 10 µL of each sample was loaded onto the center of the filter on the upper 96-well kit plate and dried in a stream of nitrogen. Subsequently, phenyl-isothiocyanate was added for derivatization. After incubation, the filter spots were dried again using an evaporator. Extraction of the metabolites was then achieved by adding 300 μL of extraction solvent. The extracts were obtained by centrifugation into the lower 96-deep well plate, followed by a dilution step with kit MS running solvent. Mass spectrometric analysis was performed on an API4000 Qtrap® tandem mass spectrometry instrument (AB Sciex, Framingham, MA) equipped with a solvent delivery system. The samples were delivered to the mass spectrometer by a LC method followed by a direct injection (DI) method. Data analysis was done using Analyst 1.6.2.

For urine organic acid, a targeted quantitative metabolomics approach was used to analyze the samples using a combination of direct injection mass spectrometry with a reverse-phase LC-MS/MS Kit. This kit, in combination with an ABI 4000 Q-Trap (Applied Biosystems/MDS Sciex) mass spectrometer, can be used for the targeted identification and quantification of 17 organic acids. The method used combines the derivatization and extraction of analytes, and the selective mass-spectrometric detection using multiple reaction monitoring (MRM) pairs. Isotope-labeled internal standards used for metabolite quantification. The kit contains a 96 deep-well collection plate, reagents and solvents used to prepare the plate assay. First 14 wells in the Kit were used for one blank, three zero samples, seven standards and three quality control samples provided with each Kit. All the samples were analyzed with the kit using the protocol described in the user manual. Briefly, samples were thawed on ice and were vortexed and centrifuged at 13,000×g. Sample and ISTD were loaded into the center of the collection well, followed by the addition of derivatization reagent. After incubation, stabilizer and water were added before LC-MS injection. Mass spectrometric analysis was performed on an API4000 Qtrap® tandem mass spectrometry instrument (AB Sciex, Framingham, MA) equipped with a solvent delivery system. The samples were delivered to the mass spectrometer by a LC method.

For urine ascorbic acid, a targeted quantitative metabolomics approach was applied to analyze the samples using a combination of direct injection mass spectrometry with a reverse-phase LC-MS/MS Kit. This kit, in combination with an ABI 4000 Q-Trap (Applied Biosystems/MDS Sciex) mass spectrometer, can be used for the targeted identification and quantification of ascorbic acid. The method used combines the extraction of analytes, and the selective mass-spectrometric detection using multiple reaction monitoring (MRM) pairs. Isotope-labeled internal standards used for metabolite quantification. The kit contains a 96 deep-well collection plate, reagents and solvents used to prepare the plate assay. First 14 wells in the Kit were used for one blank, three zero samples, seven standards and three quality control samples provided with each Kit. All the samples were analyzed with the kit using the protocol described in the user manual. Briefly, samples were thawed on ice and were vortexed and centrifuged at 13,000×g. Sample and ISTD were loaded into the center of the collection well, followed by the addition of extraction reagent. After incubation, the extracts were obtained by centrifugation into the lower 96-deep well plate. Mass spectrometric analysis was performed on an API4000 Qtrap® tandem mass spectrometry instrument (AB Sciex, Framingham, MA) equipped with a solvent delivery system. The samples were delivered to the mass spectrometer by a LC method.

For each assay, a total of 382 samples including both the CRC and control samples were randomized and analyzed using 5 plates in 96-well plate format. For each plate, a set of calibration curves was generated and used for quantification. Linear regression ($R_2$) for the calibration curves of each metabolite were >0.99 for all plates. For each plate, the LOQs were calculated to be three times the values of the matrix solutions and an average of LODs from 5 plates were reported in Table 2 and used for later analysis. Metabolite level that is lower than the LOD was unreliable and classified as missing value. A total of 46 metabolite features (including methyl-histidine, propionic acid, isobutyric acid, and 43 lipids) were removed as >50% of the information was missing (Table 2). Three QC samples were included in each 96-well plate to assess the coefficient of variation (CV %) across the 5 different plates. The CV % of QC samples for each metabolite was calculated as the standard deviation divided by the average. Notably, the CV % for each metabolite across was <15% indicating a robust analytical method.

TABLE 2

| Metabolites | | | | |
|---|---|---|---|---|
| Assay | Mode | Metabolites | LLOD (μM) | Removed due to missing values |
| PITC Assay | LC-MS | Creatinine | 1 | |
| | | Gly | 0.5 | |
| | | Ala | 1 | |
| | | Ser | 1 | |
| | | Pro | 1 | |
| | | Val | 0.5 | |
| | | Thr | 0.5 | |
| | | PEA | 0.0001 | |
| | | Taurine | 0.5 | |
| | | Putrescine | 0.0001 | |
| | | c4-OH-Pro | 0.005 | |
| | | t4-OH-Pro | 0.1 | |
| | | Leu | 1.5 | |
| | | Ile | 0.1 | |
| | | Asn | 1 | |
| | | Asp | 1 | |
| | | Gln | 1 | |
| | | Glu | 0.5 | |
| | | Met | 0.1 | |
| | | Dopamine | 0.1 | |
| | | His | 1 | |
| | | alpha-AAA | 1 | |
| | | Phe | 0.1 | |
| | | Met-SO | 0.01 | |
| | | Arg | 1 | |
| | | Ac-Orn | 0.1 | |
| | | Cit | 0.01 | |
| | | Serotonin | 0.01 | |
| | | Tyr | 0.1 | |
| | | DOPA | 0.01 | |
| | | ADMA | 1 | |
| | | total DMA | 1 | |
| | | Trp | 1 | |
| | | Kynurenine | 0.05 | |
| | | Carnosine | 0.01 | |
| | | Orn | 0.5 | |
| | | Lys | 0.1 | |
| | | Spermidine | 0.01 | |
| | | Spermine | 0.1 | |
| | | Sarcosine | 0.1 | |
| | | Diacetylspermine | 0.01 | |
| | | Tyramine | 0.1 | |
| | | Creatine | 1 | |
| | | Betaine | 1 | |
| | | Choline | 1 | |
| | | TMAO | 1 | |
| | | MethylHis | 1 | Yes |
| | FIA | LYSOC14:0 | 0.04 | |
| | | LYSOC16:1 | 0.04 | Yes |
| | | LYSOC16:0 | 0.04 | Yes |

TABLE 2-continued

Metabolites

| Assay | Mode | Metabolites | LLOD (µM) | Removed due to missing values |
|---|---|---|---|---|
| | | LYSOC17:0 | 0.04 | Yes |
| | | LYSOC18:2 | 0.04 | Yes |
| | | LYSOC18:1 | 0.04 | Yes |
| | | LYSOC18:0 | 0.04 | Yes |
| | | LYSOC20:4 | 0.04 | Yes |
| | | LYSOC20:3 | 0.04 | |
| | | LYSOC24:0 | 0.04 | Yes |
| | | LYSOC26:1 | 0.04 | Yes |
| | | LYSOC26:0 | 0.04 | Yes |
| | | LYSOC28:1 | 0.04 | Yes |
| | | LYSOC28:0 | 0.04 | Yes |
| | | 14:1SMOH | 0.025 | Yes |
| | | 16:1SM | 0.01 | Yes |
| | | 16:0SM | 0.03 | Yes |
| | | 16:1SMOH | 0.012 | Yes |
| | | 18:1SM | 0.01 | Yes |
| | | PC32:2AA | 0.09 | Yes |
| | | 18:0SM | 0.07 | Yes |
| | | 20:2SM | 0.005 | Yes |
| | | PC36:0AE | 0.09 | Yes |
| | | PC36:6AA | 0.09 | Yes |
| | | PC36:0AA | 0.09 | Yes |
| | | 22:2SMOH | 0.01 | Yes |
| | | 22:1SMOH | 0.015 | Yes |
| | | PC38:6AA | 0.09 | Yes |
| | | PC38:0AA | 0.09 | Yes |
| | | PC40:6AE | 0.09 | Yes |
| | | 24:1SMOH | 0.01 | Yes |
| | | PC40:6AA | 0.09 | Yes |
| | | PC40:2AA | 0.09 | Yes |
| | | PC40:1AA | 0.09 | Yes |
| | | C0 | 4 | |
| | | C2 | 0.15 | |
| | | C3:1 | 0.08 | Yes |
| | | C3 | 0.08 | |
| | | C4:1 | 0.03 | |
| | | C4 | 0.03 | |
| | | C3OH | 0.09 | |
| | | C5:1 | 0.03 | |
| | | C5 | 0.03 | |
| | | C4OH | 0.03 | |
| | | C6:1 | 0.035 | |
| | | C6 | 0.015 | |
| | | C5OH | 0.015 | |
| | | C5:1DC | 0.03 | |
| | | C5DC | 0.015 | |
| | | C8 | 0.17 | |
| | | C5MDC | 0.015 | |
| | | C9 | 0.04 | |
| | | C7DC | 0.035 | |
| | | C10:2 | 0.04 | |
| | | C10:1 | 0.12 | |
| | | C10 | 0.16 | |
| | | C12:1 | 0.057 | |
| | | C12 | 0.057 | |
| | | C14:2 | 0.012 | |
| | | C14:1 | 0.015 | |
| | | C14 | 0.03 | Yes |
| | | C12DC | 0.057 | Yes |
| | | C14:2OH | 0.012 | |
| | | C14:1OH | 0.015 | |
| | | C16:2 | 0.008 | |
| | | C16:1 | 0.06 | Yes |
| | | C16 | 0.018 | Yes |
| | | C16:2OH | 0.008 | |
| | | C16:1OH | 0.06 | Yes |
| | | C16OH | 0.03 | Yes |
| | | C18:2 | 0.009 | Yes |
| | | C18:1 | 0.04 | Yes |
| | | C18 | 0.02 | Yes |
| | | C18:1OH | 0.04 | Yes |
| Organic Acid | LC-MS | Glucose | 20 | |
| | | Lactic acid | 1 | |
| | | beta-Hydroxybutyric acid | 0.1 | |
| | | alpha-Ketoglutaric acid | 1 | |
| | | Citric acid | 1 | |
| | | Butyric acid | 0.005 | |
| | | Propionic acid | 0.005 | Yes |
| | | HPHPA | 0.01 | |
| | | p-Hydroxyhippuric acid | 1 | |
| | | Succinic acid | 0.1 | |
| | | Fumaric acid | 0.1 | |
| | | Pyruvic acid | 0.1 | |
| | | Isobutyric acid | 0.01 | Yes |
| | | Hippuric acid | 0.01 | |
| | | Methylmalonic acid | 0.05 | |
| | | Homovanillic acid | 0.01 | |
| | | Indole acetic acid | 0.05 | |
| | | Uric acid | 10 | |
| Ascorbic acid | LC-MS | Ascorbic acid | 1 | |

(LYSOC = lysophosphatidylcholine;
SM = sphingomyelin;
SMOH = sphingomyelin with OH group (hydroxyl);
PC = phosphatidylcholine;
C = carbon (for acylcarnitine groups), the first number means how many carbons are present in the lipids, the second number shows the saturation degree [see, e.g., LIPID MAPS Structure Database (LMSD) Lipid Classification System at www.lipidmaps.org/data/classification/LM_classification_exp.php; BIOCRATES Life Sciences AG, Annotation of potential isobaric and isomeric lipid species at www.biocrates.com/images/List-of-Isobaric-and-Isomeric-Lipid-Species.pdf])

Example 3. Potential Biomarkers for Colorectal Cancer

Figure 1B:
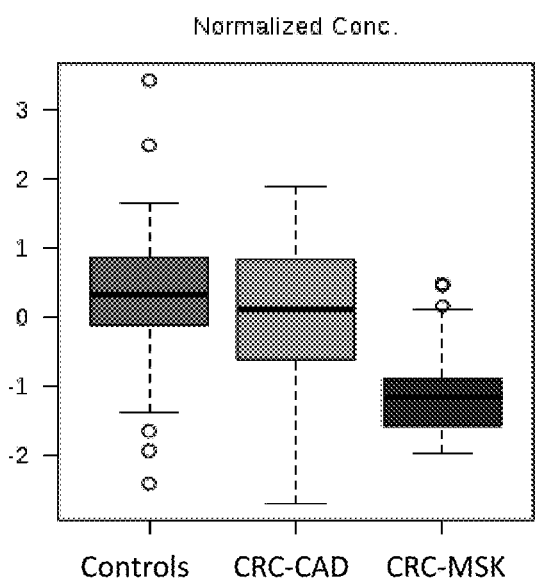
Figure 1C:
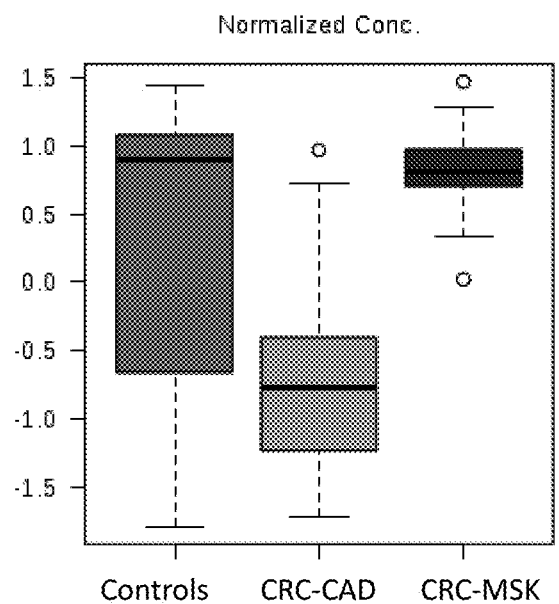
Figure 1D:
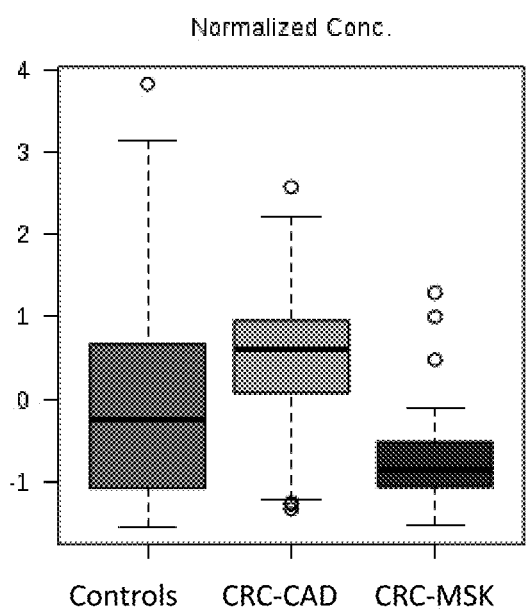
Figure 3A:
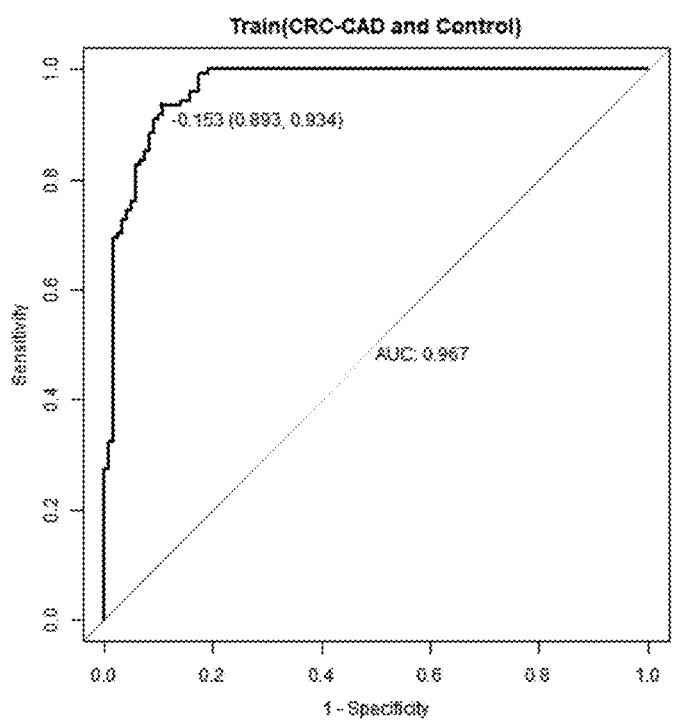
FIGS. 3A-3F are the ROC curves of Model I on training set using 17 metabolites (FIG. 3A), Model I on testing set using 17 metabolites (FIG. 3B), Model II on training set using 4 metabolites (FIG. 3C), Model II on testing set using 4 metabolites (FIG. 3D), Model III on training set using diacetylspermine and kynurenine (FIG. 3E), and Model III on testing set using diacetylspermine and kynurenine (FIG. 3F).
Figure 3B:
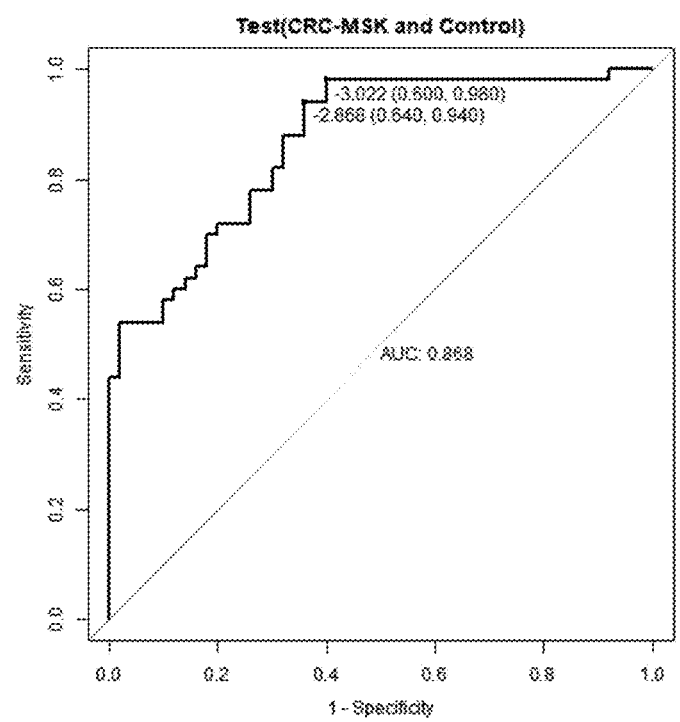

Potential biomarkers for colorectal cancer were identified by comparing the metabolomic profile from CRC versus controls for both the fold change (FC) analyses and t-tests. A total of 17 metabolites were identified by volcano plot with a threshold for fold change either >2 or <0.5 and p-valueK<0.05 (Table 3). Results from the one-way ANOVA analyses for the three study groups identified consistent markers for CRC. For each of the 17 metabolites, the level changes in either CRC group (e.g., CRC-CAD or CRC-MSK) compared to the control group were analyzed. Diacetylspermine (FIG. 1A), proline, kynurenine, and glucose were upregulated in both CRC groups compared to controls and classified as consistent biomarkers. Although they were identified as potential markers according to the volcano plot for CRC cases versus controls, the levels of 3-(3-Hydroxyphenyl)-3-hydroxypropanoic acid (TPTPA, FIG. 1B), beta-hydroxybutyric acid, 3,4-dihydroxyl phenylalanine(DOPA), 4-hydroxyproline, aminoadipic acid, putrescine, indole acetic acid, hippuric acid, citric acid, and sarcosine did not significantly change when CRC-CAD were compared to controls. Similarly, there were no significant changes in the levels of Tetradecenoyl carnitine (C14:1), and aspartic acid (FIG. 1C), and sarcosine when CRC-MSK was compared to controls. When compared against the control group, the level of butyric acid (FIG. 1D) increased in CRC-CAD and decreased in CRC-MSK. The level changes of 13 metabolites were dependent on the cohort rather than CRC status and were discarded from future analyses (Table 3).

build a model and 50 CRC-MSK and 50 Controls were used as testing set to validate the model. The first model (I) used the 17 metabolites listed in Table 3 selected according to the volcano plot of CRC versus control. This model had an area under the curve (AUC) value of 0.967 for training set and 0.868 for testing set (FIGS. 3A and 3B). At specificity of 80%, the model's sensitivity were 99.2% for training set and

TABLE 3

Potential colorectal cancer biomarkers

| | | | | Metabolite level change relative to controls | | |
| --- | --- | --- | --- | --- | --- | --- |
| Metabolite | HMDB ID | Fold Change | $p$ value | CRC-CAD | CRC-MSK | Consistent biomarker |
| 1. Diacetylspermine | HMDB02172 | 10.75 | 3.61E−31 | + | + | Yes |
| 2. Proline | HMDB00162 | 2.53 | 4.04E−31 | + | + | Yes |
| 3. C14:1 | HMDB62588 | 3.20 | 3.19E−22 | + | NC | No |
| 4. Kynurenine | HMDB00684 | 3.50 | 6.53E−16 | + | + | Yes |
| 5. Glucose | HMDB00122 | 3.06 | 1.90E−15 | + | + | Yes |
| 6. HPHPA | HMDB02643 | 0.33 | 9.44E−11 | NC | − | No |
| 7. Aspartic acid | HMDB00191 | 0.32 | 5.73E−10 | − | NC | No |
| 8. Beta-hydroxybutyric acid | HMDB00357 | 17.56 | 2.55E−09 | NC | + | No |
| 9. DOPA | HMDB00181 | 14.63 | 5.57E−09 | NC | + | No |
| 10. 4-Hydroxyproline | HMDB00725 | 2.53 | 1.31E−08 | NC | + | No |
| 11. Aminoadipic acid | HMDB00510 | 0.47 | 2.70E−08 | NC | − | No |
| 12. Putrescine | HMDB01414 | 3.78 | 1.36E−05 | NC | + | No |
| 13. Indole acetic acid | HMDB00197 | 0.21 | 2.06E−04 | NC | − | No |
| 14. Hippuric acid | HMDB00714 | 0.39 | 4.42E−04 | NC | − | No |
| 15. Citric acid | HMDB00094 | 3.07 | 1.18E−03 | NC | + | No |
| 16. Sarcosine | HMDB00271 | 14.68 | 1.82E−03 | NC | NC | No |
| 17. Butyric acid | HMDB00039 | 0.19 | 9.72E−03 | + | − | No |

Abbreviations:
"+" indicates a significant (P value < 0.05) metabolite level increase;
"−" indicates a significant metabolite level decrease;
"NC" means that the metabolite level was not significantly changed.

Example 4. Prediction Models

Figure 2A:
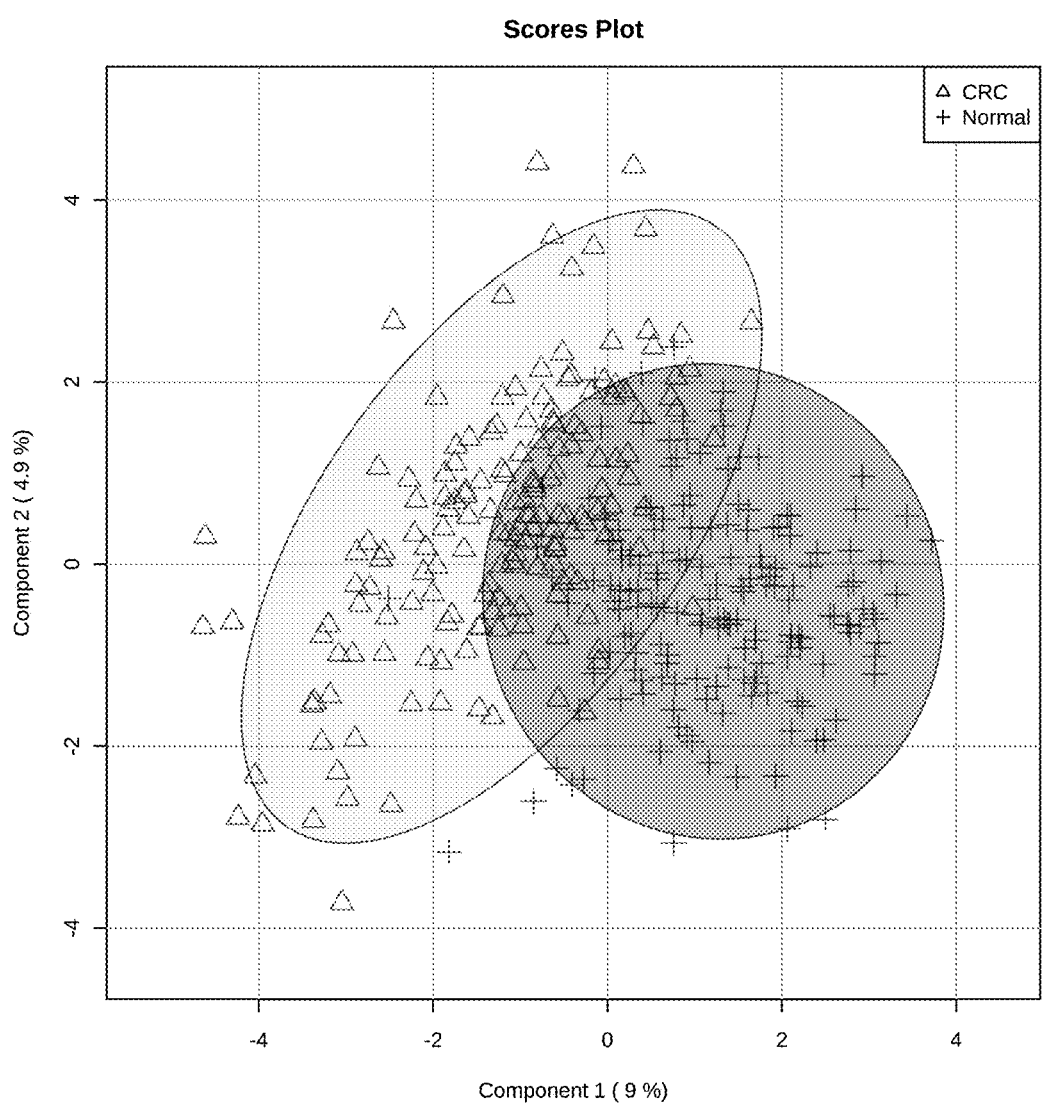
FIGS. 2A-2C are results showing separation plot from sPLS-DA with component 1 and component 2 (FIG. 2A); variables selected by the sPLS-DA model for a component 1 (FIG. 2B); and variables selected by the sPLS-DA model for a component 2 (FIG. 2C).
Figure 2B:
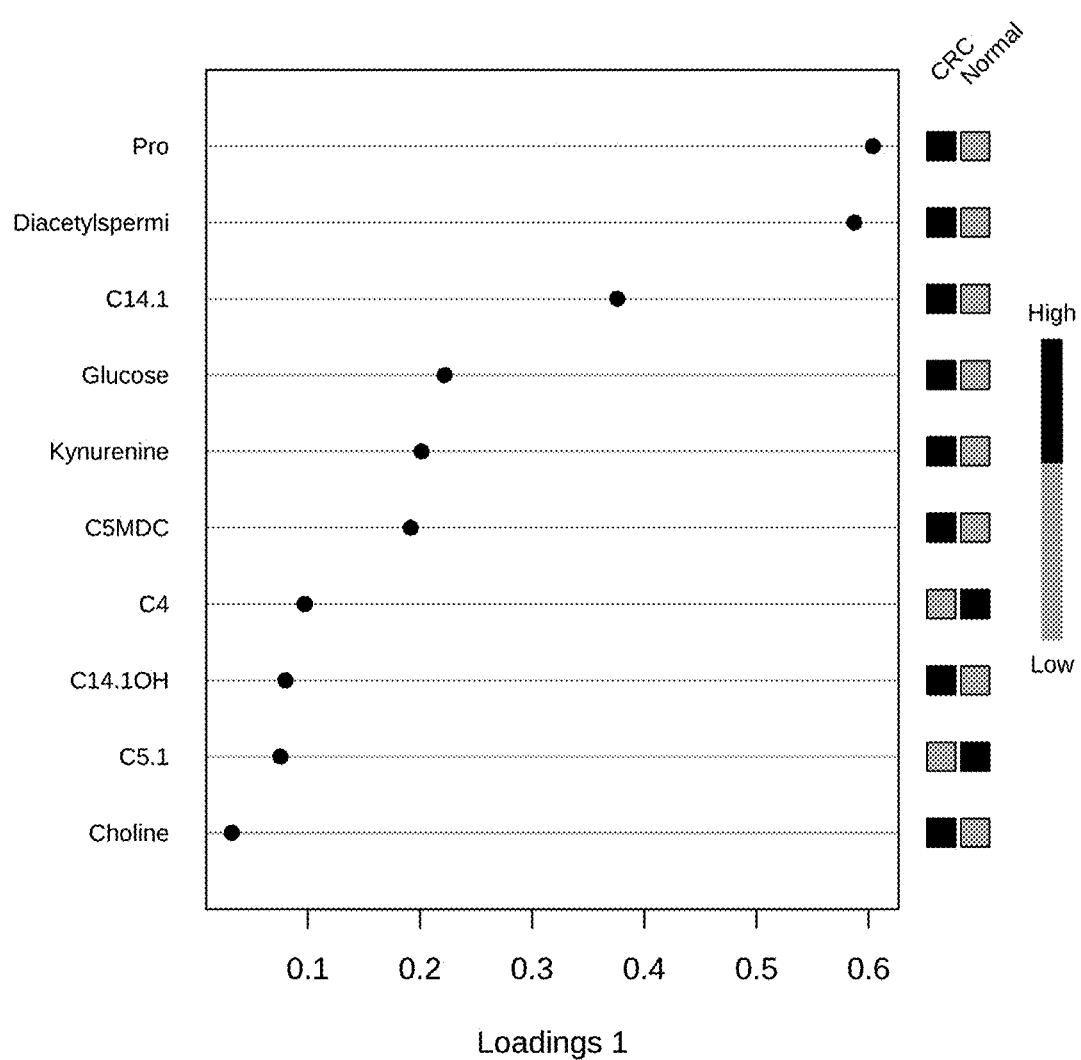
Figure 2C:
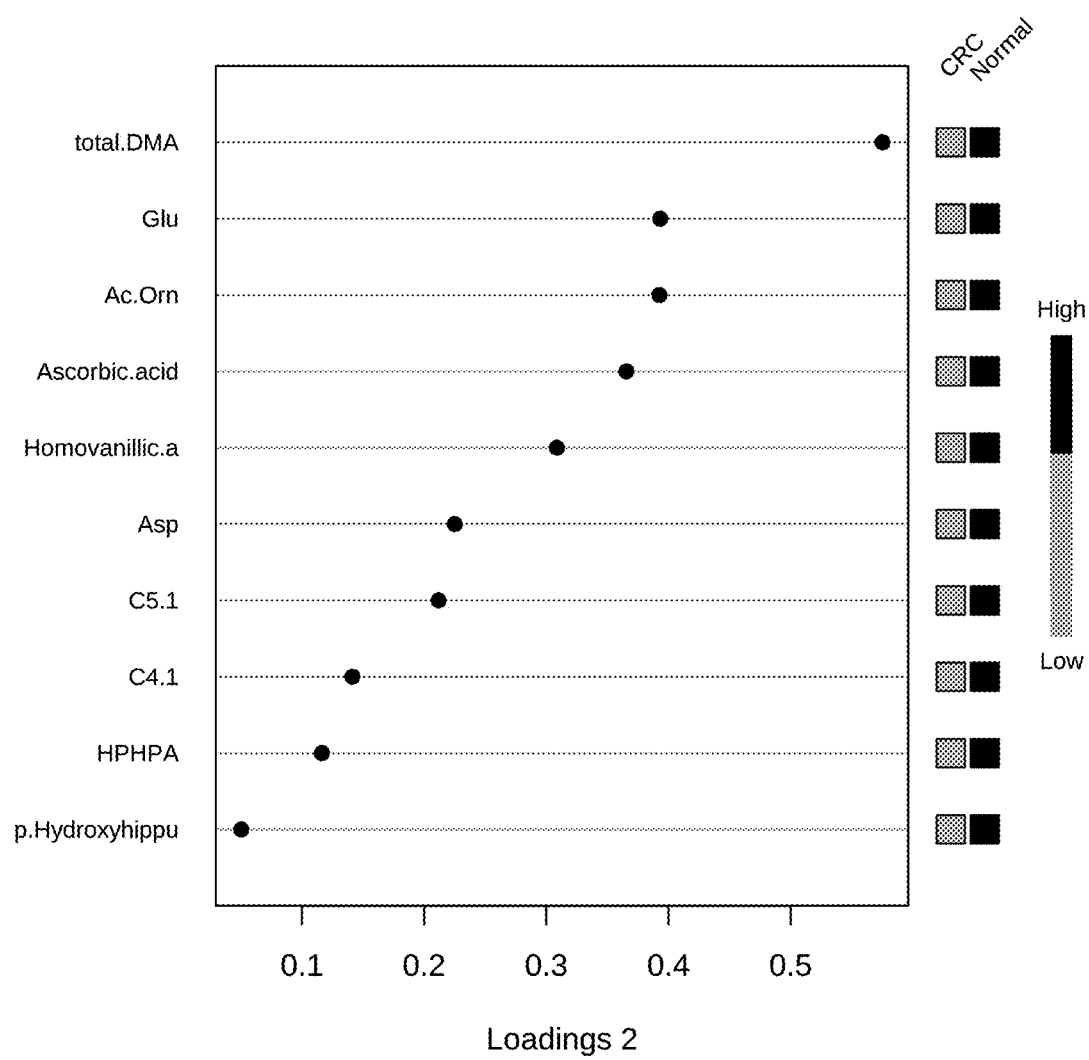

To construct an effective diagnostic model for CRC, multivariate analysis was conducted using MetaboAnalyst. Among the PCA, PLS-DA, and sPLS-DA model options, sPLS-DA provided the best separation between the groups with the least number of metabolites. FIG. 2A shows the separation plot from sPLS-DA with component 1 and component 2. The classification error rate was 11.4%. The metabolites selected by the sPLS-DA model for component 1 and component 2 with their loading value are shown in FIGS. 2B and 2C. Notably, diacetylspermine, proline, kynurenine, and glucose were among the top 6 selected features based on loading values for component 1. This confirms their selection as consistent markers.

Figure 3C:
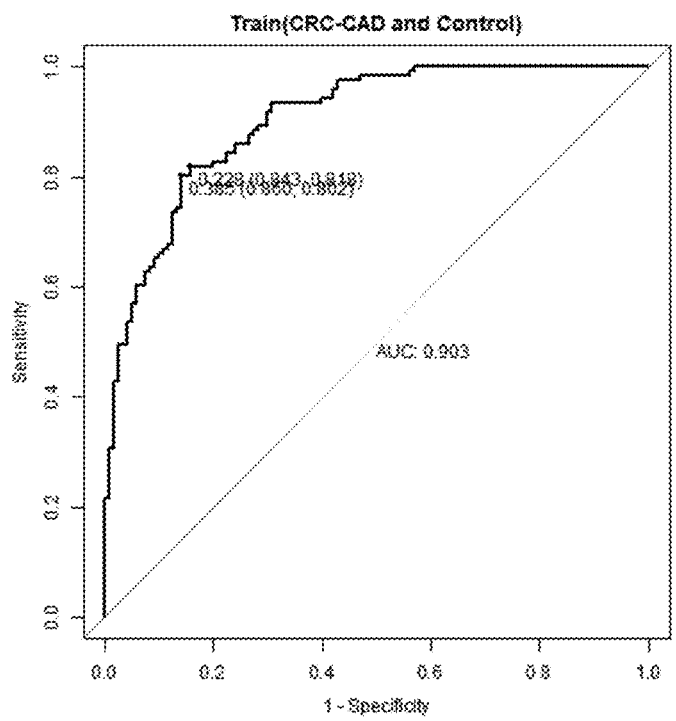
Figure 3D:
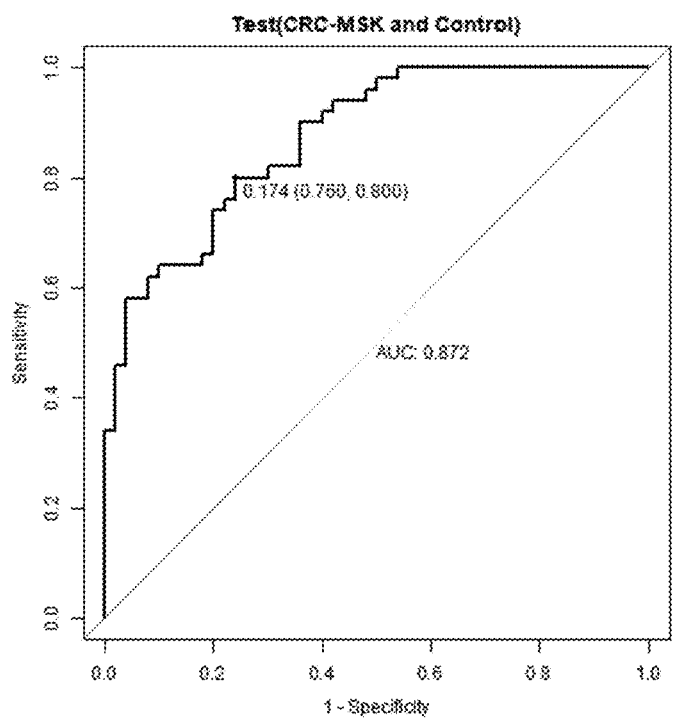
Figure 3E:
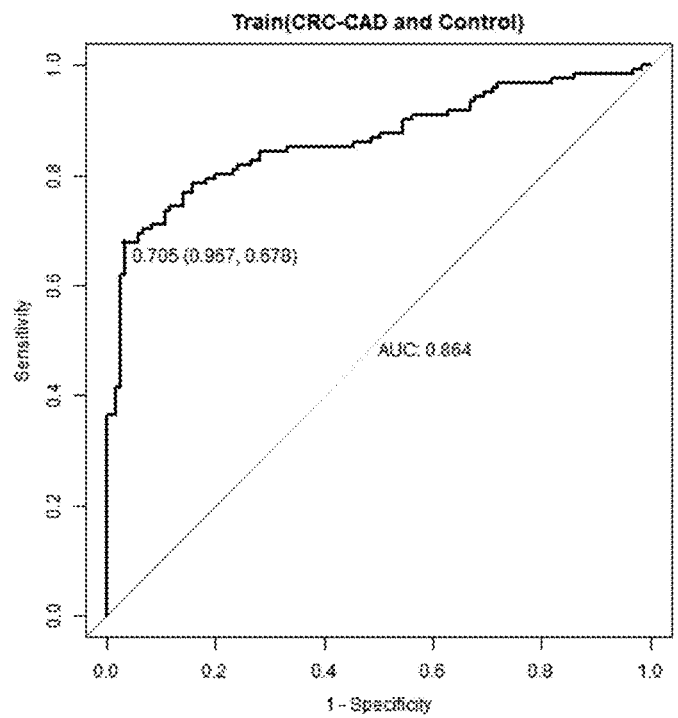
Figure 3F:
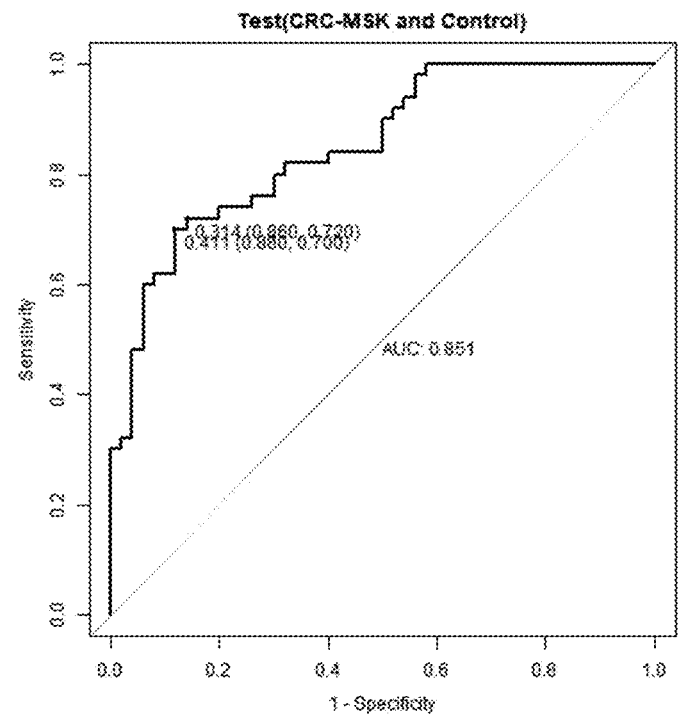

Finally, logistic regression models were constructed in R with selected metabolites. A leave-out approach was used to build and evaluate models as it is most rigorous. 121 CRC-CAD and 121 Controls were used as training set to 74.0% for testing set, respectively (Table 4). The second model (II) was limited to the four metabolites (e.g., proline, diacetylspermine, kynurenine, and glucose) identified as robust CRC biomarkers from the ANOVA analysis. The model had an AUC of 0.903 for training set and an AUC of 0.873 on testing set (FIGS. 3C and 3D) with a training sensitivity of 82.6% and a testing sensitivity of 72.% at specificity of 80% (Table 4). The last logistic regression model (III) incorporated only diacetylspermine and kynurenine. Proline and glucose were excluded due to their potential association with diet (39), a feature that was not controlled during the 24 hours prior to urine sample collection. With an AUC of 0.868 on training set and an AUC of 0.851 on testing set (FIGS. 3E and 3F), model III has the least AUC drop from training to testing among 3 models which confirmed the robustness of the selected biomarkers. At specificity of 80%, model III's sensitivity were 80.0% for training set and 74.0% for testing set, respectively (Table 4).

TABLE 4

The AUC of the ROC curve, sensitivity, and specificity for each model

| Logistic regression models | Features | AUC | | | Sensitivity at specificity of 80% | | |
|---|---|---|---|---|---|---|---|
| | | Train | Test | Delta (Train-Test) | Train | Test | Delta (Train-Test) |
| I | Proline, Diacetylspermine, C14.1, Kynurenine, Glucose, Aspartic acid, Glutamate, Beta-Hydroxybutyric acid, HPHPA, DOPA, c4-OH.Proline, Putrescine, Indole acetic acid, Citric acid, Hippuric acid, Sarcosine, and Butyric acid | 0.967 | 0.868 | 0.099 | 99.2% | 74.0% | 25.2% |
| II | Proline, Diacetylspermine Kynurenine, and Glucose | 0.903 | 0.873 | 0.030 | 82.6% | 72.0% | 10.6% |
| III | Diacetylspermine and Kynurenine | 0.864 | 0.851 | 0.013 | 80.0% | 74.0% | 6.0% |

As demonstrated above, the inventors have identified a discrete subset of common urinary metabolites that may serve as potential biomarkers for CRC when used in combination based upon modelling to separate CRC and control samples. An sPLS-DA model with two components was built with a classification error rate of 11.4%. For logistic models, the AUC varied from 0.965 to 0.868 highlighting the predictive power of urinary metabolomics for CRC screening. However, given the sample size (n=342), one needs to be conscientious about error due to overfitting the model. To guard against this, further analyses were performed by building a model that only used consistent biomarkers regardless of the cohorts. Finally, a metabolomic predictor for CRC was built with two metabolites: diacetylspermine and kynurenine. At its optimal cut-off value of 0.498, the predictor's specificity and sensitivity values were 90.6% and 74.3%, respectively.

Figure 4A:
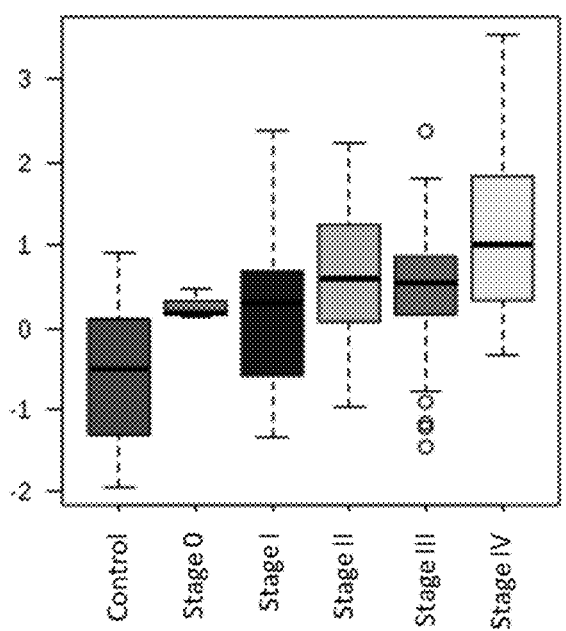
FIGS. 4A-4B show the normalized level trend for diacetylspermine (FIG. 4A) and kynurenine (FIG. 4B) from controls, to Stage 0, to Stage I, to Stage II, to stage III and to Stage IV.
Figure 4B:
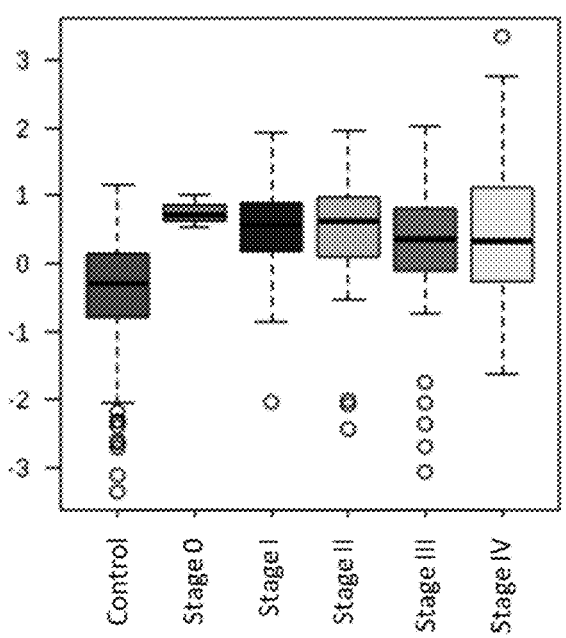

Although the mechanism of diacetylspermine and kynurenine being CRC markers still needs to be investigated, their association with the presence of CRC is clear. Here, the trend of their changes was plotted from control, to stage 0, to stage I, to stage II, to stage III, to stage IV in FIG. 4. For both diacetylspermine and kynurenine, the biggest change was observed from control to stage 0 confirming the usage of these two markers for early screening. There was a continuous increase in diacetylspermine as the cancer progresses.

Knowing more about the metabolic cycles and degradation pathways involved in CRC will be helpful to identify additional biomarkers. The specificity of the metabolite profile can also be evaluated by comparing with samples from patients with other cancer types. In addition, it may be beneficial to make a more comprehensive metabolomic assessment. This could be done using additional analytical assays, such as gas chromatography-mass spectrometry (GC-MS), which will enable the detection of more metabolites (48). A more comprehensive metabolomic profile may improve diagnostic accuracy. Larger data sets supported by comprehensive clinicodemographic characteristics can be also valuable to discern the discrete shifts in metabolites associated with real time changes in cellular metabolism associated with disease. This can also facilitate external validation of putative biomarker panels such as that reported herein.

In the study described herein, patients were not asked to follow a controlled diet or fast before providing a urine sample. Appreciating the diurnal changes in urinary metabolite levels (49), all collections were completed during daytime business hours. Dietary controls place unreasonable burdens on patients and believed that this would decrease the value of this or any urinary biomarker panel intended for use as a screening tool for CRC. Further, it is highly probable that differences in the intestinal microbiota between healthy individuals and those with CRC impact urinary metabolites more so than diet (50).

A limitation of any large multicenter study is the need to handle, ship, and store the biosamples over time. To minimize metabolite degradation, all specimens were handled similarly regardless of collection date and aliquoting prior to the first freeze at −80° C. prevented exposure to multiple free-thaw cycles (51,52).

In conclusion, metabolomic-based biomarkers for CRC identified in this study have potential clinical application for population-based CRC screening using urine, a preferred biosample that is readily available, straightforward to collect as part of any physician's clinic visit, and acceptable to patients in most cultures. Further supporting the use of urine is availability of collection, handling, shipping, and storage protocols many of which have been instituted by major biobanks and repositories.

For statistical analysis performed in the Examples above, data pre-processing was performed using code written in R, version 3.4.3 (30). Metabolites that were lower than the LLOD or not detected in more than half of the urine samples were removed from the initial list of 140 metabolites. For the remaining metabolites on the list, if a sample had a metabolite level that was less than the LLOD, it was replaced with half the value of the LLOD. Statistical analyses were conducted with MetaboAnalyst, version 4.0 for the web (31). Metabolite level was normalized against creatinine, log-transformed, and auto-scaled. Potential biomarkers for CRC were identified (32) by comparing the metabolomic profiles of the CRC and control groups for both fold-change analyses and Student t-tests. One-way ANOVA was performed on the independent sample groups (e.g., CRC-CAD, CRC-MSK, and control) to identify statistically significant metabolite differences (33-35). The metabolites with level changes in the same direction for both the CRC-CAD and CRC-MSK groups were considered consistent CRC markers. Furthermore, multivariate models, using principal component analysis (PCA), partial least squares—discriminant analysis (PLS-DA), and sparse PLS-DA (sPLS-DA) (36) were constructed. Finally, predictors were built using the logistic regression with selected biomarkers. Leave-out approach was used to evaluate the built models. 171 Controls were randomized to form 121 Controls for training and 50 Controls for testing with balanced age, gender and smoking status. 121 CRC-CAD and 121 Controls were used as training set to build a model, and 50 CRC-MSK and 50 Controls were used as testing set to validate the model.

All code for statistical analyses was also written in R, version 3.4.3 (30). The glmnet package was used for logistic regression (37). Receiver operating characteristic (13) curves were generated and reported using the ROCR package (38).

REFERENCES

1. Ferlay J, Ervik M, Lam F, Colombet M, Mery L, Pineros M, et al. 2018 Oct. 19, 2018.
   Global Cancer Observatory: Cancer Tomorrow. International Agency for Research on Cancer <https://gco.iarc.fr/tomorrow>. Oct. 19, 2018.
2. Levin T R, Corley D A, Jensen C D, Schottinger J E, Quinn V P, Zauber A G, et al. Effects of Organized Colorectal Cancer Screening on Cancer Incidence and Mortality in a Large Community-Based Population. Gastroenterology 2018 doi 10.1053/j.gastro.2018.07.017.
3. Dube C. Organized screening is better than opportunistic screening at decreasing the burden of colorectal cancer in the United States. Gastroenterology 2018; 155(5):1302-4 doi 10.1053/j.gastro.2018.10.010.
4. Navarro M, Nicolas A, Ferrandez A, Lanas A. Colorectal cancer population screening programs worldwide in 2016: An update. World J Gastroenterol 2017; 23(20): 3632-42 doi 10.3748/wjg.v23.i20.3632.
5. Schreuders E H, Ruco A, Rabeneck L, Schoen R E, Sung J J, Young G P, et al. Colorectal cancer screening: a global overview of existing programmes. Gut 2015; 64(10): 1637-49 doi 10.1136/gutjnl-2014-309086.
6. Imperiale T F, Ransohoff D F, Itzkowitz S H, Levin T R, Lavin P, Lidgard G P, et al. Multitarget Stool DNA Testing for Colorectal-Cancer Screening. New England Journal of Medicine 2014; 370(14):1287-97 doi 10.1056/NEJMoa1311194.
7. Quintero E, Castells A, Bujanda L, Cubiella J, Salas D, Lanas A, et al. Colonoscopy versus fecal immunochemical testing in colorectal-cancer screening. N Engl J Med 2012; 366(8):697-706 doi 10.1056/NEJMoa1108895.
8. van Roon A H, Goede S L, van Ballegooijen M, van Vuuren A J, Looman C W, Biermann K, et al. Random comparison of repeated faecal immunochemical testing at different intervals for population-based colorectal cancer screening. Gut 2013; 62(3):409-15 doi 10.1136/gutjnl-2011-301583.
9. Zubero M B, Arana-Arri E, Pijoan J I, Portillo I, Idigoras I, Lopez-Urrutia A, et al. Population-based colorectal cancer screening: comparison of two fecal occult blood test. Frontiers in pharmacology 2014; 4:175 doi 10.3389/fphar.2013.00175.
10. Singh H, Bernstein C N, Samadder I N, Ahmed R. Screening rates for colorectal cancer in Canada: a cross-sectional study. CMAJ open 2015; 3(2):E149-57 doi 10.9778/cmajo.20140073.
11. Singal A G, Corley D A, Kamineni A, Garcia M, Zheng Y, Doria-Rose P V, et al. Patterns and predictors of repeat fecal immunochemical and occult blood test screening in four large health care systems in the United States. Am J Gastroenterol 2018; 113(5):746-54 doi 10.1038/s41395-018-0023-x.
12. Church J. Complications of Colonoscopy. Gastroenterology Clinics of North America 2013; 42(3):639-57 doi 10.1016/j.gtc.2013.05.003.
13. Dougherty M K, Brenner A T, Crockett S D, Gupta S, Wheeler S B, Coker-Schwimmer M, et al. Evaluation of Interventions Intended to Increase Colorectal Cancer Screening Rates in the United States: A Systematic Review and Meta-analysis. JAMA internal medicine 2018 doi 10.1001/jamainternmed.2018.4637.
14. Cossu G, Saba L, Minerba L, Mascalchi M. Colorectal Cancer Screening: The Role of Psychological, Social and Background Factors in Decision-making Process. Clinical practice and epidemiology in mental health: CP & EMH 2018; 14:63-9 doi 10.2174/1745017901814010063.
15. Osborne J M, Flight I, Wilson C J, Chen G, Ratcliffe J, Young G P. The impact of sample type and procedural attributes on relative acceptability of different colorectal cancer screening regimens. Patient preference and adherence 2018; 12:1825-36 doi 10.2147/ppa.S172143.
16. Liles E G, Coronado G D, Perrin N, Harte A H, Nungesser R, Quigley N, et al. Uptake of a colorectal cancer screening blood test is higher than of a fecal test offered in clinic: A randomized trial. Cancer Treatment and Research Communications 2017; 10:27-31 doi https://doi.org/10.1016/j.ctarc.2016.12.004.
17. Lamb Y N, Dhillon S. Epi proColon((R)) 2.0 CE: A Blood-Based Screening Test for Colorectal Cancer. Molecular diagnosis & therapy 2017; 21(2):225-32 doi 10.1007/s40291-017-0259-y.
18. Anabtawi A, Mathew L M. Improving compliance with screening of diabetic patients for microalbuminuria in primary care practice. ISRN endocrinology 2013; 2013: 893913 doi 10.1155/2013/893913.
19. Oboler S K, Prochazka A V, Gonzales R, Xu S, Anderson R J. Public expectations and attitudes for annual physical examinations and testing. Annals of internal medicine 2002; 136(9):652-9.
20. Widlak M M, Neal M, Daulton E, Thomas C L, Tomkins C, Singh B, et al. Risk stratification of symptomatic patients suspected of colorectal cancer using faecal and urinary markers. Colorectal disease: the official journal of the Association of Coloproctology of Great Britain and Ireland 2018 doi 10.1111/codi.14431.
21. Guo C, Xie C, Chen Q, Cao X, Guo M, Zheng S, et al. A novel malic acid-enhanced method for the analysis of 5-methyl-2'-deoxycytidine, 5-hydroxymethyl-2'-deoxycytidine, 5-methylcytidine and 5-hydroxymethylcytidine in human urine using hydrophilic interaction liquid chromatography-tandem mass spectrometry. Analytica chimica acta 2018; 1034:110-8 doi 10.1016/j.aca.2018.06.081.
22. Nakajima T, Katsumata K, Kuwabara H, Soya R, Enomoto M, Ishizaki T, et al. Urinary Polyamine Biomarker Panels with Machine-Learning Differentiated Colorectal Cancers, Benign Disease, and Healthy Controls. International journal of molecular sciences 2018; 19(3) doi 10.3390/ijms19030756.
23. Venalainen M K, Roine A N, Hakkinen M R, Vepsalainen J J, Kumpulainen P S, Kiviniemi M S, et al.

Altered Polyamine Profiles in Colorectal Cancer. Anticancer research 2018; 38(6):3601-7 doi 10.21873/anticanres.12634.
24. Wang H, Tso V, Wong C, Sadowski D, Fedorak R N. Development and validation of a highly sensitive urine-based test to identify patients with colonic adenomatous polyps. Clin Transl Gastroenterol 2014; 5:e54 doi 10.1038/ctg.2014.2.
25. Deng L, Chang D, Foshaug R R, Eisner R, Tso V K, Wishart D S, et al. Development and Validation of a High-Throughput Mass Spectrometry Based Urine Metabolomic Test for the Detection of Colonic Adenomatous Polyps. Metabolites 2017; 7(3):32 doi 10.3390/metabo7030032.
26. Deng L, Fang H, Tso V K, Sun Y, Foshaug R R, Krahn S C, et al. Clinical validation of a novel urine-based metabolomic test for the detection of colonic polyps on Chinese population. Int J Colorectal Dis 2017; 32(5): 741-3 doi 10.1007/s00384-016-2729-9.
27. Tso V E R, Macleod S, Ismond K P, Foshaug R R, Wang H, Joseph R, Chang D, Taylor N and Fedorak R N. Consistency of Metabolite Determination from NMR Spectra over Time and Between Operators. Metabolomics 2015; 5(3):151 doi 10.4172/2153-0769.1000151.
28. Eisner R, Greiner R, Tso V, Wang H, Fedorak R N. A machine-learned predictor of colonic polyps based on urinary metabolomics. Biomed Res Int 2013; 2013: 303982 doi 10.1155/2013/303982.
29. Wong C K, Fedorak R N, Prosser C I, Stewart M E, van Zanten S V, Sadowski D C. The sensitivity and specificity of guaiac and immunochemical fecal occult blood tests for the detection of advanced colonic adenomas and cancer. Int J Colorectal Dis 2012; 27(12):1657-64 doi 10.1007/s00384-012-1518-3.
30. R Core Team. 2018 R: A Language and Environment for Statistical Computing. R Foundation for Statistical Computing <https://www.R-project.org>.
31. Chong J, Soufan O, Li C, Caraus I, Li S, Bourque G, et al. MetaboAnalyst 4.0: towards more transparent and integrative metabolomics analysis. Nucleic Acids Research 2018; 46(W1):W486-W94 doi 10.1093/nar/gky310.
32. Altobelli E, Angeletti P M, Latella G. Role of Urinary Biomarkers in the Diagnosis of Adenoma and Colorectal Cancer: A Systematic Review and Meta-Analysis. Journal of Cancer 2016; 7(14):1984-2004 doi 10.7150/jca.16244.
33. Qiu G, Zheng Y, Wang H, Sun J, Ma H, Xiao Y, et al. Plasma metabolomics identified novel metabolites associated with risk of type 2 diabetes in two prospective cohorts of Chinese adults. International Journal of Epidemiology 2016; 45(5):1507-16 doi 10.1093/ije/dyw221.
34. Stoessel D, Stellmann J-P, Willing A, Behrens B, Rosenkranz S C, Hodecker S C, et al. Metabolomic Profiles for Primary Progressive Multiple Sclerosis Stratification and Disease Course Monitoring. Frontiers in human neuroscience 2018; 12:226-doi 10.3389/fnhum.2018.00226.
35. Delplancke T D J, de Seymour J V, Tong C, Sulek K, Xia Y, Zhang H, et al. Analysis of sequential hair segments reflects changes in the metabolome across the trimesters of pregnancy. Scientific reports 2018; 8(1):36-doi 10.1038/s41598-017-18317-7.
36. Lê Cao K-A, Boitard S, Besse P. Sparse PLS discriminant analysis: biologically relevant feature selection and graphical displays for multiclass problems. BMC Bioinformatics 2011; 12(1):253 doi 10.1186/1471-2105-12-253.
37. Friedman J H, Hastie T, Tibshirani R. Regularization Paths for Generalized Linear Models via Coordinate Descent. Journal of Statistical Software 2010; 33(1):1-22 doi 10.18637/jss.v033.i01.
38. Sing T, Sander O, Beerenwinkel N, Lengauer T. ROCR: visualizing classifier performance in R. Bioinformatics 2005; 21(20):3940-1 doi 10.1093/bioinformatics/bti623.
39. Cifuentes A. Foodomics: Advanced Mass Spectrometry in Modern Food Science and Nutrition. Wiley; 2013.
40. Spacek M. Kynurenine in disease, with particular reference to cancer. Canadian Medical Association journal 1955; 73(3):198-201.
41. Enjoji M, Nakamuta M, Arimura E, Morizono S, Kuniyoshi M, Fukushima M, et al. Clinical significance of urinary N1,N12-diacetylspermine levels in patients with hepatocellular carcinoma. The International journal of biological markers 2004; 19(4):322-7.
42. Hiramatsu K, Takahashi K, Yamaguchi T, Matsumoto H, Miyamoto H, Tanaka S, et al. N(1),N(12)-Diacetylspermine as a sensitive and specific novel marker for early- and late-stage colorectal and breast cancers. Clinical cancer research: an official journal of the American Association for Cancer Research 2005; 11(8):2986-90 doi 10.1158/1078-0432.Ccr-04-2275.
43. Yamaguchi K, Nakamura M, Shirahane K, Konomi H, Torata N, Hamasaki N, et al. Urine diacetylspermine as a novel tumour maker for pancreatobiliary carcinomas. Digestive and liver disease: official journal of the Italian Society of Gastroenterology and the Italian Association for the Study of the Liver 2005; 37(3):190-4 doi 10.1016/j.dld.2004.10.006.
44. Takahashi Y, Sakaguchi K, Horio H, Hiramatsu K, Moriya S, Takahashi K, et al. Urinary N1, N12-diacetylspermine is a non-invasive marker for the diagnosis and prognosis of non-small-cell lung cancer. Br J Cancer 2015; 113(10):1493-501 doi 10.1038/bjc.2015.349.
45. Stejskal D, Humenanska V, Hanulova Z, Fiala R, Vrtal R, Solichova P, et al. Evaluation of urine N1,N12-Diacetylspermine as potential tumor marker for urinary bladder cancer. Biomed Pap Med Fac Univ Palacky Olomouc Czech Repub 2006; 150(2):235-7.
46. Zhang F, Zhang Y, Zhao W, Deng K, Wang Z, Yang C, et al. Metabolomics for biomarker discovery in the diagnosis, prognosis, survival and recurrence of colorectal cancer: a systematic review. Oncotarget 2017; 8(21): 35460-72 doi 10.18632/oncotarget.16727.
47. Liang P S, Chen T Y, Giovannucci E. Cigarette smoking and colorectal cancer incidence and mortality: systematic review and meta-analysis. International journal of cancer 2009; 124(10):2406-15doi10.1002/ijc.24191.
48. Bathe O F, Shaykhutdinov R, Kopciuk K, Weljie A M, McKay A, Sutherland F R, et al. Feasibility of identifying pancreatic cancer based on serum metabolomics. Cancer Epidemiology Biomarkers & Prevention 2011; 20(1): 140-7 doi 10.1158/1055-9965.Epi-10-0712.
49. Ni Y, Xie G, Jia W. Metabonomics of Human Colorectal Cancer: New Approaches for Early Diagnosis and Biomarker Discovery. Journal of Proteome Research 2014; 13(9):3857-70 doi 10.1021/pr500443c.
50. Erben V, Bhardwaj M, Schrotz-King P, Brenner H. Metabolomics biomarkers for detection of colorectal neoplasms: a systematic review. Cancers 2018; 10(246):1-24 doi 10.3390/cancers10080246.
51. Rotter M, Brandmaier S, Prehn C, Adam J, Rabstein S, Gawrych K, et al. Stability of targeted metabolite profiles of urine samples under different storage conditions. Metabolomics 2017; 13(1):4 doi 10.1007/s11306-016-1137-z.

52. Laparre J, Kaabia Z, Mooney M, Buckley T, Sherry M, Le Bizec B, et al. Impact of storage conditions on the urinary metabolomics fingerprint. Analytica chimica acta 2017; 951:99-107 doi 10.1016/j.aca.2016.11.055.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

The invention claimed is:

1. A method for determining the presence of colorectal cancer (CRC) and/or colorectal polyps in a subject, said method comprising:
   (a) obtaining a first metabolite profile from a first bodily fluid sample collected from the subject, wherein said first metabolite profile is obtained by measuring the level of each metabolite within the metabolite profile in the sample, and wherein the metabolite profile comprises diacetylspermine and kynurenine;
   (b) comparing said first metabolite profile with a reference metabolite profile;
   (c) detecting at least 2-fold increase of the level of diacetylspermine and the level of kynurenine as compared to the corresponding levels in the reference metabolite profile, thereby detecting the presence of CRC and/or colorectal polyps in the subject; and
   (d) performing a surgical removal of CRC tumor and/or colorectal polyp in the subject determined to have CRC and/or colorectal polyps.

2. The method of claim 1, wherein the metabolite profile further comprises proline and glucose and wherein step (c) further comprises detecting the presence of colorectal cancer (CRC) and/or colorectal polyps in the subject when the level of proline is increased at least 2-fold and the level of glucose is increased at least 2-fold as compared to the corresponding level(s) in the reference metabolite profile.

3. The method of claim 1, wherein the metabolite profile further comprises one or more metabolites selected from tetradecenoyl carnitine (C14:1), 3-(3-Hydroxyphenyl)-3-hydroxypropanoic acid (HPHPA), aspartic acid, beta-hydroxybutyric acid, 3,4-dihydroxyl phenylalanine (DOPA), 4-hydroxyproline, aminoadipic acid, putrescine, indole acetic acid, hippuric acid, citric acid, sarcosine, and butyric acid.

4. The method of claim 1, wherein the reference metabolite profile is obtained from similarly processed bodily fluid samples of healthy subjects which do not have colorectal cancer (CRC) and colorectal polyps.

5. The method of claim 4, wherein said reference metabolite profile is obtained from healthy subjects which do not have colorectal cancer (CRC) and colorectal polyps as determined by colonoscopy.

6. The method of claim 4, wherein said reference metabolite profile is obtained from healthy subjects which are matched to the subject being tested by age and/or gender.

7. The method of claim 1, wherein step (b) involves the use of one or more methods selected from a multivariate statistical analysis, logistic regression, principal component analysis (PCA), partial least squares discriminant analysis (PLS-DA), sparse PLS-DA (sPLS-DA), orthogonal partial least squares discriminant analysis (oPLS-DA), support vector machines (SVM), discriminant analysis, kernel methods, nonparametric methods, tree-based methods, generalized linear models, generalized additive modes, fuzzy logic based methods, neural networks, and genetic algorithm-based methods.

8. The method of claim 1, wherein the subject does not have symptoms of colorectal cancer (CRC) and/or colorectal polyps.

9. The method of claim 1, wherein the method further comprises administering to the subject one or more additional diagnostic tests selected from fecal occult blood test (FOBT), fecal immunochemical test (FIT), fecal DNA tests, flexible sigmoidoscopy, blood septin 9 tests, air-contrast barium enema, computed tomography colonography (CTC), and colonoscopy.

10. The method of claim 1, further comprising enrolling the subject in a clinical trial.

11. The method of claim 1, wherein, prior to measuring metabolite levels, the bodily fluid sample(s) is refrigerated, frozen, dried, treated by administering an anti-bacterial agent, treated by administering an antifungal agent, or any combination thereof.

12. The method of claim 1, wherein the levels of the metabolites are measured using one or more methods selected from nuclear magnetic resonance (NMR) spectroscopy, liquid chromatography-mass spectrometry (LC-MS), reverse-phase liquid chromatography-mass spectrometry (LC-MS), direct injection mass spectrometry, high performance liquid chromatography (HPLC), gas chromatography, thin layer chromatography, electrochemical analysis, mass spectroscopy, refractive index spectroscopy, ultraviolet spectroscopy, fluorescent analysis, radiochemical analysis, near-infrared spectroscopy, gas chromatography, impedance analysis, colorimetric analysis, and light scattering analysis.

13. The method of claim 1, wherein the subject is human.

14. The method of claim 1, wherein the subject is an experimental or a veterinary animal.

15. The method of claim 1, wherein the bodily fluid sample is selected from urine, blood, serum, and saliva.

16. A method for treating colorectal cancer (CRC) and/or colorectal polyps in a subject, said method comprising:
   (a) obtaining a first metabolite profile from a first bodily fluid sample collected from the subject, wherein said first metabolite profile is obtained by measuring the level of each metabolite within the metabolite profile in the sample, wherein the metabolite profile comprises diacetylspermine and kynurenine;
   (b) comparing said first metabolite profile with a reference metabolite profile;
   (c) detecting at least 2-fold increase of the level of diacetylspermine and the level of kynurenine as compared to the corresponding levels in the reference metabolite profile, thereby detecting the presence of CRC and/or colorectal polyps in the subject; and
   (d) performing a surgical removal of CRC tumor and/or colorectal polyp in the subject.

* * * * *